United States Patent
Fisher et al.

(10) Patent No.: US 11,880,989 B2
(45) Date of Patent: Jan. 23, 2024

(54) IMAGING ABNORMALITIES IN VASCULAR RESPONSE

(71) Applicant: THORNHILL SCIENTIFIC INC., Toronto (CA)

(72) Inventors: Joseph Fisher, Thornhill (CA); Olivia Sobczyk, Etobicoke (CA); Adrian P. Crawley, Toronto (CA); Julien Poublanc, Toronto (CA); Kevin Sam, Toronto (CA); Daniel M. Mandell, Toronto (CA); David Mikulis, Oakville (CA); James Duffin, Toronto (CA)

(73) Assignee: THORNHILL SCIENTIFIC INC., North York (CA)

( * ) Notice: Subject to any disclaimer, the term of this patent is extended or adjusted under 35 U.S.C. 154(b) by 908 days.

(21) Appl. No.: 15/332,567

(22) Filed: Oct. 24, 2016

(65) Prior Publication Data

US 2017/0236294 A1    Aug. 17, 2017

Related U.S. Application Data

(63) Continuation-in-part of application No. 14/859,809, filed on Sep. 21, 2015, now Pat. No. 10,791,931, and
(Continued)

(51) Int. Cl.
*G06T 7/38* (2017.01)
*A61B 5/00* (2006.01)
(Continued)

(52) U.S. Cl.
CPC .............. *G06T 7/38* (2017.01); *A61B 5/0042* (2013.01); *A61B 5/0263* (2013.01);
(Continued)

(58) Field of Classification Search
CPC .............. G06T 7/11; G06T 2207/10072; G06T 2207/30096; G06T 2207/30101;
(Continued)

(56) References Cited

U.S. PATENT DOCUMENTS

2003/0139659 A1 *   7/2003   Dale ..................... A61B 5/055
                                                              600/407
2004/0161138 A1 *   8/2004   Ashton .................... G06T 7/11
                                                              382/128
(Continued)

FOREIGN PATENT DOCUMENTS

CA      2419622      9/2003
WO      WO02/01242   1/2002
(Continued)

OTHER PUBLICATIONS

Spano et al. "CO2 Blood Oxygen Level - dependent MR Mapping of Cerebrovascular Reserve in a Clinical Population: Safety, Tolerability, and Technical Feasibility". Radiology; vol. 266: No. 2; Feb. 2013 (Year: 2013).*
(Continued)

*Primary Examiner* — Ashley K Buran
*Assistant Examiner* — Helene Bor
(74) *Attorney, Agent, or Firm* — Perry + Currier Inc.

(57) ABSTRACT

Z maps combined with a standardized stimulus in the form of a targeted arterial partial pressures of carbon dioxide provide surprisingly enhanced images for the assessment of pathological CVR. For example, the z-map assessment of patients with known steno-occlusive diseases of the cervicocerebral vasculature showed an enhanced resolution of the presence, localization, and severity of the pathological CVR. Z-map have been found to be useful to reduce the confounding effects of test-to-test, subject-to-subject, and platform-to-platform variability for comparison of CVR images
(Continued)

Related U.S. Application Data a continuation of application No. PCT/CA2015/000274, filed on Apr. 27, 2015, said application No. 14/859,809 is a continuation of application No. 14/614,310, filed on Feb. 4, 2015, now abandoned.

(60) Provisional application No. 61/984,617, filed on Apr. 25, 2014.

(51) Int. Cl.
| | |
|---|---|
| *A61B 5/145* | (2006.01) |
| *G06T 7/00* | (2017.01) |
| *G06T 7/11* | (2017.01) |
| *A61B 5/026* | (2006.01) |
| *A61B 5/055* | (2006.01) |
| *A61B 5/0205* | (2006.01) |

(52) U.S. Cl.
CPC ........ *A61B 5/14542* (2013.01); *G06T 7/0012* (2013.01); *G06T 7/11* (2017.01); *A61B 5/0205* (2013.01); *A61B 5/026* (2013.01); *A61B 5/055* (2013.01); *A61B 5/4064* (2013.01); *A61B 2576/026* (2013.01); *G06T 2207/10088* (2013.01); *G06T 2207/30016* (2013.01); *G06T 2207/30104* (2013.01)

(58) Field of Classification Search
CPC . G06T 2207/30016; G06T 2207/30104; G06T 2207/10088; G06T 7/38; G06T 7/0012; A61B 5/72; A61B 5/742; A61B 5/743; A61B 6/032; A61B 6/461; A61B 6/504; A61B 6/507; A61B 6/5217; A61B 8/06; A61B 8/461; A61B 8/5207; A61B 5/055; A61B 8/0891; A61B 8/483; A61B 8/5223; A61B 5/4064; A61B 5/026; A61B 5/0205; A61B 2576/026; A61B 5/14542; A61B 5/0263; A61B 5/0042
See application file for complete search history.

(56) References Cited

U.S. PATENT DOCUMENTS

| | | | | |
|---|---|---|---|---|
| 2006/0104494 | A1* | 5/2006 | Collins | G06T 7/0012 |
| | | | | 382/128 |
| 2007/0019846 | A1* | 1/2007 | Bullitt | G06T 7/0014 |
| | | | | 382/128 |
| 2007/0036402 | A1* | 2/2007 | Cahill | G06T 7/0012 |
| | | | | 382/128 |
| 2007/0225606 | A1 | 9/2007 | Naghavi et al. | |
| 2008/0275340 | A1 | 11/2008 | Beach et al. | |
| 2010/0244834 | A1* | 9/2010 | Mori | G06T 7/11 |
| | | | | 324/318 |
| 2011/0160543 | A1* | 6/2011 | Parsey | A61B 6/501 |
| | | | | 600/300 |
| 2013/0010927 | A1 | 1/2013 | Seppi et al. | |
| 2014/0003701 | A1* | 1/2014 | Masood | A61B 6/504 |
| | | | | 382/134 |

FOREIGN PATENT DOCUMENTS

| | | |
|---|---|---|
| WO | WO-2004073779 A2 | 9/2004 |
| WO | WO2007/012197 | 2/2007 |
| WO | WO2011/143751 | 11/2011 |
| WO | WO2012/130248 | 10/2012 |
| WO | WO2013/030743 | 3/2013 |
| WO | WO-2013138910 A1 | 9/2013 |
| WO | WO-2013163735 A1 * | 11/2013 ........ A61M 16/0045 |
| WO | WO-2014194401 A1 | 12/2014 |

OTHER PUBLICATIONS

Kassner et al. "Blood-Oxygen Level Dependent MRI Measures of Cerebrovascular Reactivity Using a Controlled Respiratory Challenge: Reproducibility and Gender Differences". Journal of Magnetic Resonance Imaging 31:298-304 (2010) pp. 298-304. (Year : 2010).*
Fierstra et al. "Topical Review Measuring cerebrovascular reactivity: what stimulus to use?". J physio; vol. 591: No. 23, p. 5809-5821; Sep. 30, 2013 (Year: 2013).*
The FIL Methods Group. "Statistical Parametric Mapping." The Wellcome Centre for Human Neuroimaging (UCL), Functional Imaging Laboratory, Oct. 1, 2014, URL: https://www.fil.ion.ucl.ac.uk/spm/.
USPTO, Notice of Allowance and Fee(5) Due, dated Nov. 20, 2019, re U.S. Appl. No. 14/859,809.
Ashburner, John, and K. Friston. "Multimodal image coregislration and partitioning—a unified framework." Neuroimage 6.3 (1997): 209-217.
Balucani, Clotilde, et al. "Cerebral hemodynamics and cognitive performance in bilateral asymptomatic carotid stenosis." [Abstract Only] Neurology 79.17 (2012): 1788-1795.
Cox, Robert W. "AFNI: software for analysis and visualization of functional magnetic resonance neuroimages." Computers and Biomedical research 29.3 (1996): 162-173.
Fierstra, Jorn, et al. "Severely impaired cerebrovascular reserve in patients with cerebral proliferative angiopathy." Journal of Neurosurgery: Pediatrics 8.3 (2011): 310-315.
FierstraA, Jorn, et al. "Non-invasive accurate measurement of arterial PCO 2 in a pediatric animal model." [Abstract Only] Journal of clinical monitoring and computing 27.2 (2013): 147-155.
Guimond, Alexandre, Jean Meunier, and Jean-Philippe Thirion. "Average brain models: A convergence study." Computer vision and image understanding 77.2 (2000): 192-210.
Han, Jay S., et al. "BOLD-MRI cerebrovascular reactivity findings in cocaine-induced cerebral vasculitis." Nature Reviews Neurology 4.11 (2008): 628.
Han, Jay S., et al. "Measurement of cerebrovascular reactivity in pediatric patients with cerebral vasculopathy using blood oxygen level-dependent MRI." Stroke 42.5 (2011): 1261-1269.
Mikulis, David J., et al. "Preoperative and postoperative mapping of cerebrovascular reactivity in moyamoya disease by using blood oxygen level-dependent magnetic resonance imaging." [Abstract Only] Journal of neurosurgery 103.2 (2005): 347-355.
Seitz, R. J., et al. "Accuracy and precision of the computerized brain atlas programme for localization and quantification in positron emission tomography." Journal of Cerebral Blood Flow & Metabolism 10.4 (1990): 443-457.
Mark, Clarisse I., et al. "Precise control of end-tidal carbon dioxide and oxygen improves BOLD and ASL cerebrovascular reactivity measures." Magnetic resonance in medicine 64.3 (2010): 749-756.
Sobczyk, Olivia, et al. "A conceptual model for CO2-induoed redistribution of cerebral blood flow with experimental confirmation using BOLD MRI." Neuroimage 92 (2014): 56-68.
Tzeng, Yu-Chieh, et al. "Assessment of cerebral autoregulalion: the quandary of quantification." American Journal of Physiology—Heart and Circulatory Physiology 303.6 (2012): H658-H671.
Webb, Jocasta, et al. "Automatic detection of hippocampal atrophy on magnetic resonance images." [Abstract Only] Magnetic Resonance Imaging 17.8 (1999): 1149-1161.
White, Nicole D. "Increasing Naloxone Access and Use to Prevent Opioid Overdose Death and Disability." American journal of lifestyle medicine 13.1 (2019): 33-35.
International Search Report on corresponding PCT application (PCT/CA2015/000274) from International Searching Authority (CIPO) dated Jul. 17, 2015.

(56) References Cited

OTHER PUBLICATIONS

Written Opnion on corresponding PCT application (PCT/CA2015/000274) from International Searching Authority (CIPO) dated Jul. 17, 2015.

Nadkarni et al. Usage of fMRI for pre-surgical planning in brain tumor and vascular lesion patients: task and statistical threshold effects on language lateralization.: Neuroimage Clin. Dec. 24, 2014; 7:415-23. doi: 10.1016/j.nicl.2014.12.014.eCollection 2015. PMID: 25685705; http://www.ncbi.nlm.nih.gov/pmc/articles/PMC4310930/pdf/main.pdf.

Sam et al. "Assessing the Effect of Unilateral Cerebral Revascularisation on the Vascular Reactivity of the Non-Intervened Hemisphere: A Retrospective Observational Study." BMJ Open 5.2 (2015): e006014. PMC. Published: Feb. 11, 2015; http://www.ncbi.nlm.nih.gov/pmc/articles/PMC4325130/pdf/bmjopen-2014-006014.pdf.

Sobczyk et al. Assessing cerebrovascular reactivity abnormality by comprision to a reference atlas.: Journal of Cerebral Blood Flow & Metabolism [serial online]. Feb. 2015; 35(2):213-220. Academic Search Research & Development, Ipswich, MA.; https://search.ebscohost.com/login.aspx?direct=true&db=asr&AN=100713008.

Spano et al. "CO2 blood oxygen level-dependent MR mapping of cerebrovascular reserve in a clinical population: safety, tolerability, and technical feasibility." Radiology. Feb. 2013; 266(2):592-598. doi: 10.1148/radiol.12112795. Epub Nov. 30, 2012; http://pubs.rsna.org/doi/pdf/10.1148/radiol.12112795.

Terashima et al. "Noninvasive assessment of coronary vasodilation using magnetic resonance angiography." J Am Coll Cardio. 2005; 45(1); 104-110. doi: 101016/j.jacc.2004.09.057. http://content/onlinejacc.org/article.aspx?articleid=1136202.

Wise et al. "Measurement of OEF and Absolute CMRO2: MRI-Based Methods Using Interleaved and Combined Hypercapnia and Hyperoxia." NeuroImage 83 (2013): Dec. 2013, pp. 1-31. http://www.ncbi.nlm.nih.gov/pmc/articles/PMC4151288/pdf/ernss-60178.pdf.

* cited by examiner

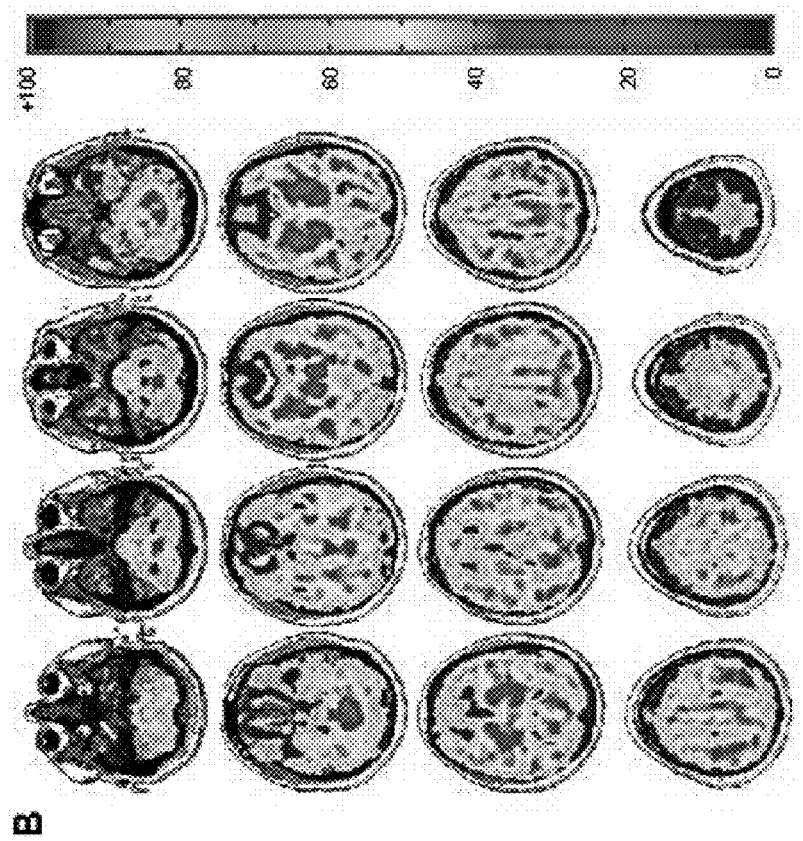
Fig. 1

Table 2

| Subject | Detailed Diagnosis | CVR map and z-map Description |
|---|---|---|
| 1 | Previous Hx of stroke. Presented with R TIAs. Angiography shows R and ICA occlusion & VA stenosis. | The CVR map shows steal in R MCA & PCA territories. The z-maps show not only the extent, but severity of abnormality. The lowest z scores correspond to the "blue" of the CVR; the z-map confirms that the CVR in the WM on the left side is also diffusely reduced. |
| 2 | R TIA presentation. Angiography shows 100% L ICA occlusion. | The CVR map shows that steal is present in the entire left hemisphere. The z-maps indicate the severity of the abnormality and the extent of hemodynamic involvement. The CVR in the R hemisphere also appears reduced. [[REF Sam]] |
| 3 | TIA. L ICA stenosis. | Despite the unilateral vascular lesion, the CVR map is symmetrical, but appears reduced. The z-maps confirm marked reduction in CVR throughout the cortex and deep WM regions. |
| 4 | Hx previous stroke. L ICA stenosis. | The CVR map appears to be normal except for a mild CVR impairment in the area of the stroke. The z-maps confirm that CVR is normal in the normal-appearing areas of the CVR map; severe reduction of CVR in area of stroke. |
| 5 | Stroke in the watershed area extending into the MCA. Stroke in the left subcortical region. Left cavernous ICA occlusion and R ICA stenosis. | The CVR map appears to be normal with possibly some reduction in the left subcortical area. The z-maps confirmed the normality of much of the scan but show that the subtle-appearing changes of the CVR map are in fact severely abnormal. |
| 6 | Hx astrocytoma of the optic chiasm as a child, Rx with surgical resection, chemotherapy and radiotherapy. L EC-IC bypass 2 y ago for MM. | The CVR map appears to be close to normal but gives an impression that CVR was somewhat diffusely reduced with little visible steal. The z-maps emphasize that there are widespread reductions in CVR and indicate their severity, particularly in the R WM region which was not apparent from the CVR. Note despite the severity of reductions in CVR, the necessary conditions to generate steal were not met. [[Sobczyk 14]] |

FIG. 6A

Table 2 (continued)

| Subject | Detailed Diagnosis | CVR map and z-map Description |
|---|---|---|
| 7 | Hx of repeat TIAs. | The CVR map shows impaired CVR in the right MCA, which extends to the ACA territory, with the severity difficult to judge; CVR elsewhere appears normal. The z-maps scores the severity and extent of reduced CVR in the area of steal, but shows the extent of impaired CVR exceeds that of steal; confirms normal reactivity in the contralateral hemisphere on the side of the EC-IC bypass. |
| 8 | Hx MM with intraventricular hemorrhage. | The CVR map shows that CVR is reduced globally, with reduced CVR and possibly some steal evident on the left. The z-maps show that the bilateral CVR impairment in both R and L MCA territories is severe beyond 2 SD. |
| 9 | Hx MM with infarct. Post R EC-IC bypass; rescanned for assessment of continuing TIA. | The CVR map indicates a persistent reduction of CVR throughout the R MCA region. The z-maps confirm these bilateral reductions in CVR, much worse in the areas of steal. |
| 10 | idiopathic intracranial hypertension. | The CVR map shows areas of steal in the WM of the frontal and occipital lobes, with normal appearing CVR in the rest of the brain. The z-maps, however, confirm bilateral severe reduction in CVR in deep GM and WM, that was not appreciated from an examination of the CVR map. |

(Abbreviations: ACA, anterior cerebral artery, EC-IC, external carotid to internal carotid GM, gray matter; Hx, History; ICA, internal carotid artery; L, Left; R right; MCA, middle cerebral artery; MM, Moyamoya; PCA, posterior cerebral artery; SD, standard deviation; TIA, transient ischemic attach; VA, vertebral artery; WM, white matter).

FIG. 6B

Table 3: Summary of comparison of CVR and its z-maps:

|  | CVR | z-map |
|---|---|---|
| sensitivity | Low: mainly identifies presence/absence of steal. | Higher sensitivity by detecting graded reductions in CVR short of steal. |
| specificity | High: steal is accepted sign of abnormal vasculature. | Lower specificity mitigated by i) normalization of CVR to normal range for region highlights abnormal CVR; ii) confluence of reduced z scores is statistically unlikely in tissue with normal CVR |
| location specific | No: CVR maps score absolute values of CVR. | Yes: z score normalizes CVR for anatomical location. |
| identify distribution of abnormality | Identifies only the distribution where steal occurs as abnormal | Identifies the distributions of various grades of reduced CVR beyond that of steal. |
| platform specific | No: can be performed on any magnet. | Probably: each platform may require its unique atlas. |
| comparison across platforms | Possibly: requires, at a minimum, standardized MR sequences and uniform stimulus *across* platforms | Yes: requires only consistency of sequences and stimulus between atlas and patient *within* each platform: z values should then be comparable across platforms. |

Fig. 7

Bland-Altmann plots of CVR for between-day reproducibility for gray (a) and white (b) matter regions.

Table 1: Demographic of healthy subject atlas.

| | | Number |
|---|---|---|
| Age Range | 20-30 | 24 |
| | 30-40 | 10 |
| | 40-50 | 5 |
| | 50-60 | 2 |
| | 60-70 | 3 |
| | 70+ | 2 |
| Sex | F | 16 |
| | M | 30 |

Fig.12

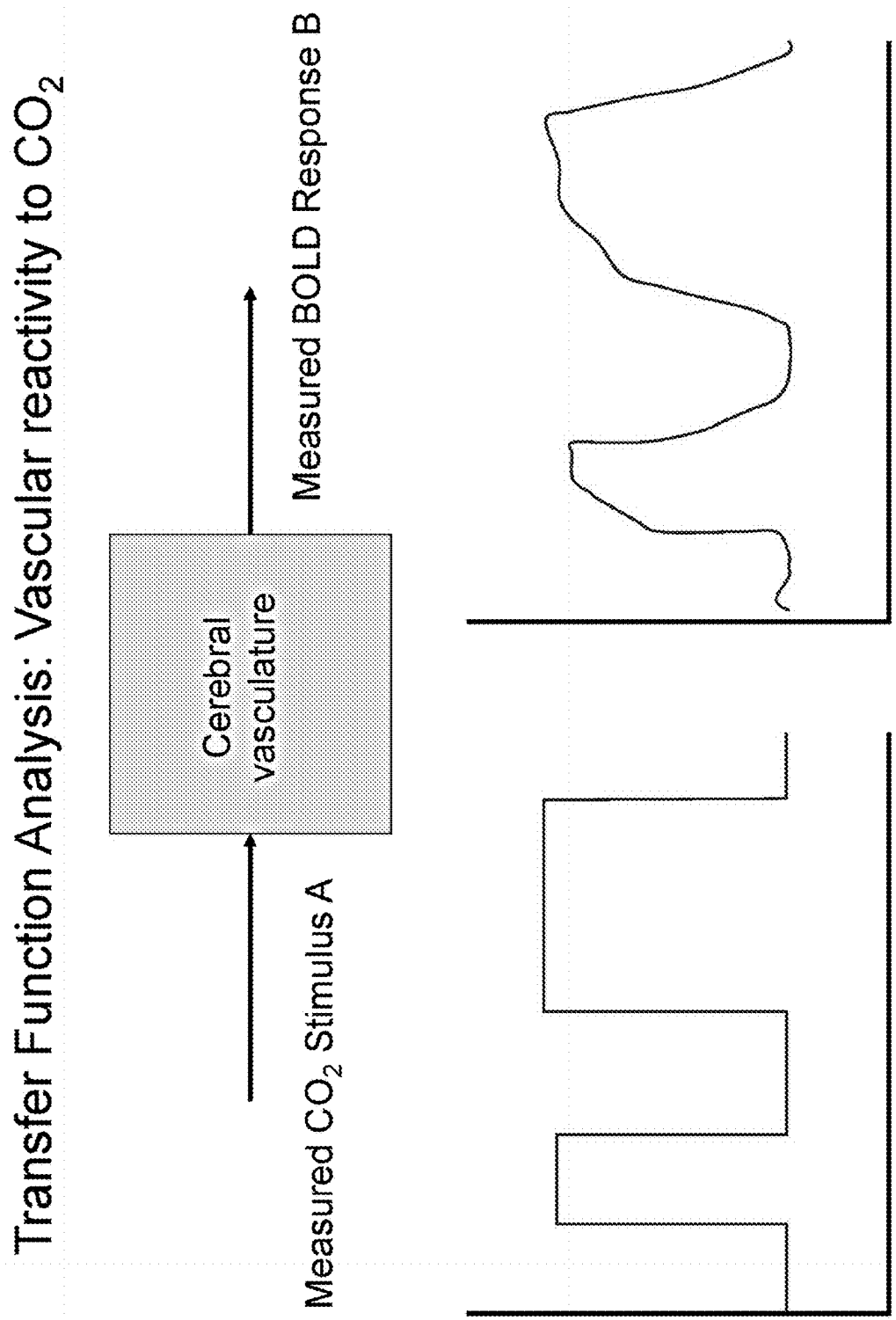

Table 4

| Step | Step Description | Step Function |
|---|---|---|
| CVR1 | Generate Stimulus | Use RespirAct to generate a standardised $P_{ET}CO_2$ stimulus sequence |
| CVR2 | Image Acquisition | A 3.0-Tesla HDx scanner using an 8-channel phased-array receiver coil (Signa; GE Healthcare, Milwaukee, Wisconsin) was used for MRI; consisting of BOLD acquisitions with echo planar imaging (EPI) gradient echo (TR/TE = 2000/30 ms, 3.75 x 3.75 x 5 mm voxels, field of view 24x24 cm, 39 slices, slice thickness 5mm, matrix size 64x64, number of frames = 254, flip angle (FA) = 85°) |
| CVR3 | Image Registration (e.g. AFNI software) | BOLD images are volume registered and slice-time corrected followed by volume re-registration for motion correction and co-registered to an axial 3-D T1-weighted Inversion-Recovery prepared Fast Spoiled Gradient-Echo (IR-FSPGR) volume (TI/TR/TE = 450/8/3 ms, voxel size 0.86 x 0.86 x 1.0 mm, matrix size 256 x 256, field of view 22 x 22 cm, slice thickness = 1mm, FA = 15°) that was acquired at the same time) |
| CVR4 | Re-Sample Stimulus (e.g. AFNI/MatLab software) | $P_{ET}CO_2$ stimulus recording was re-sampled and interpolated at the BOLD sampling frequency of 0.5 Hz |
| CVR5 | Align Stimulus and Response (e.g. AFNI software) | $P_{ET}CO_2$ stimulus is time-aligned to the point of maximum correlation with the whole brain average BOLD signal |
| CVR6 | Linear Fit Stimulus vs. Response (e.g. AFNI software) | A linear, least-squares fit of the BOLD signal with the $P_{ET}CO_2$ stimulus provides the slope measure (CVR) on a voxel-by-voxel basis |
| CVR7 | Generate CVR map (e.g. AFNI software) | Generate CVR map images and extrapolate to fit and align with anatomical images |
| CVR8 | Display CVR Map (e.g. AFNI software) | Show CVR maps data overlaid on anatomical images |
| CVR9 | Export Data (e.g. AFNI software) | Export map data from AFNI for Transfer Function Analysis |

Figure 17b

Table 5

| Step | Step Description | Step Function |
|---|---|---|
| Z1 | Import Data | Import CVR map data exported from AFNI for the Atlas cohort of normal healthy subjects |
| Z2 | Anatomical Standardisation (e.g. AFNI/SPM8/MatLab software) | From the healthy cohort, each of the individual subject's T1-weighted fast-spoiled gradient echo brain volumes was co-registered into MNI (Montreal Neurological Institute) standard space, as defined by a T1-weighted MNI152 standard template using a 12-parameter 23 affine transformation followed by nonlinear deformations. The calculated transformation for each individual was then applied to the BOLD data and a spatial smoothing of full-width half-maximum 5mm was applied to each voxel |
| Z3 | Calculation of Mean and Standard Deviation (e.g. AFNI software) | The mean ($\mu$) and associated standard deviation ($\sigma$) of the healthy cohort CVR for each voxel was calculated to form the normal CVR atlas |
| Z4 | Patient Anatomical Standardisation (e.g. SPM8/MatLab software) | Spatial normalization of the individual patient's anatomic scan and CVR map using a MNI152 SPM distributed template |
| Z5 | Calculate z-score (e.g. AFNI software) | The patient's CVR of each voxel (x) was scored in terms of a z-value (i.e., $z=(x-\mu)/\sigma$) |
| Z6 | Colour Scaling (e.g. AFNI software) | A color was assigned to each z-score to indicate the direction and magnitude (in z-values) of the differences from the mean of the corresponding atlas voxel) |
| Z7 | Display z-map (e.g. AFNI software) | To display the patient's z-map as colour-coded values superimposed upon the anatomical scan |

Figure 18b

Table 6

| Step | Step Description | Step Function |
|---|---|---|
| Tau 1 | Import Data (e.g. MatLab software) | Import (BOLD) response to a stimulus ($CO_2$) image data from AFNI |
| Tau 2 | Model Response (e.g. MatLab software) | The response to a stimulus is modeled as the stimulus convolved with a hemodynamic response function (HRF) of the cerebrovasculat blood vessels. HRF was an exponential decay function of the form: $\exp(-t/\tau)$, where t is the time variable and $\tau$ the time constant. The HRF parameters are a time constant $\tau$, representing the speed of response, and the asymptote A of the exponential response, representing the amplitude of response |
| Tau 3 | Construct set of model responses (e.g. MatLab software) | A set of multiple model responses are constructed for $\tau$ ranging from 2 to 100 s, in 2 s increments |
| Tau 4 | Select best fit model response (e.g. AFNI software) | The maximal correlation coefficient between the measured response for each voxel and one of the multiple response model determines the best fit and the amplitude, A, and time constant, $\tau$ for the voxel |
| Tau 5 | Display Maps (e.g. AFNI software) | Display the amplitude and time constant maps as colour-coded values superimposed upon the anatomical scans |

Figure 19b

Table 7

| Step | Step Description | Step Function |
|---|---|---|
| TFA 1 | Import Data (LabVIEW software) | Import (BOLD) response to a stimulus ($CO_2$) image data from AFNI |
| TFA 2 | Calculate Average Response (LabVIEW software) | Average the responses for all voxels |
| TFA 3 | Align stimulus and average response (LabVIEW software) | Align the average response and the stimulus by eye using the graphical interface. Re-sample $P_{ET}CO_2$ if necessary. |
| TFA 4 | Welch Averaging (LabVIEW software) | For each voxel the stimulus and response signals data arrays are split up into segments of a given length, and overlapped by 50%. In our case the 500 s data arrays are split into 5 segments and with the overlapping provides a Welch average of 9. |
| TFA 5 | Transfer Function Analysis (LabVIEW software) | The frequency response function, defined as the Welch average cross-spectrum of the response signal divided by the Welch average autospectrum of the stimulus signal, yields gain and phase measures. Gain is the magnitude of the response to the stimulus and Phase is the speed of response) |
| TFA 6 | Calculate Coherence (LabVIEW software) | Coherence, an indication of the causality linking the stimulus-response relationship is calculated from Welch averages of the cross- and auto- spectra as the average cross-spectrum squared divided by the product of the stimulus and response autospectra. |
| TFA 7 | Export Data (LabVIEW software) | Export the Gain, Phase and Coherence voxel data in AFNI compatible format. |
| TFA 8 | Display Data (AFNI software) | Display the Gain, Phase and Coherence maps as colour-coded values superimposed upon the anatomical scans. |

Figure 20b

Table 8

| Step | Step Description | Step Function |
|---|---|---|
| IDZ1 | Import Data | Import CVR map data exported from AFNI for the ID Atlas cohort of normal healthy subjects. |
| IDZ2 | Anatomical Standardisation (AFNI/SPM8/MatLab software) | From the healthy cohort, each of the individual subject's T1-weighted fast-spoiled gradient echo brain volumes was co-registered into MNI (Montreal Neurological Institute) standard space, as defined by a T1-weighted MNI152 standard template using a 12-parameter 23 affine transformation followed by nonlinear deformations. The calculated transformation for each individual was then applied to the BOLD data and a spatial smoothing of full-width half-maximum 5mm was applied to each voxel. |
| IDZ3 | Calculate Interval Difference (ID) Maps (AFNI software) | For each individual of the ID atlas cohort the MNI registered individual CVR maps measured at two time points were subtracted to form an ID CVR map. |
| IDZ4 | Calculate ID Mean and Standard Deviation (AFNI software) | The mean ($\mu$) and associated standard deviation ($\sigma$) of the healthy cohort ID CVR for each voxel was calculated to form the normal ID CVR atlas. |
| IDZ5 | Patient Anatomical Standardisation (AFNI/SPM8/MatLab software) | Spatial normalization of the individual patient's anatomic scan and CVR maps using a MNI152 SPM distributed template. |
| IDZ6 | Calculate Patient Interval Difference Map (AFNI software) | The MNI registered patient CVR maps measured at two time points were subtracted to form the patient's ID CVR map. |
| IDZ7 | Calculate ID z-score (AFNI software) | The Patient's ID CVR of each voxel (x) was scored in terms of a z-value (i.e., $z=(x-\mu)/\sigma$). |
| IDZ8 | Colour Scaling (AFNI software) | A color was assigned to each z-score to indicate the direction and magnitude (in z-values) of the differences from the mean of the corresponding atlas voxel. |
| IDZ9 | Display ID z-map (AFNI software) | To display the patient ID z-map as colour-coded values superimposed upon the anatomical scan. |

Figure 21b

IMAGING ABNORMALITIES IN VASCULAR RESPONSE

CROSS-REFERENCE TO RELATED APPLICATIONS

This application is a Continuation of co-pending International Application No. PCT/CA2015/000274, filed Apr. 27, 2015, the disclosure of which is incorporated herein by reference. International Application No. PCT/CA2015/000274, in turn, claims the benefit, under 35 U.S.C. § 119(e), of U.S. provisional application Ser. No. 61/984,617, filed on Apr. 25, 2014, the disclosure of which is incorporated herein by reference in its entirety. This application is also a Continuation-in-Part of co-pending U.S. patent application Ser. No. 14/859,809, filed Sep. 21, 2015, which is a Continuation of U.S. patent application Ser. No. 14/614,310, filed Feb. 4, 2015, the disclosures of which are hereby incorporated by reference as if set forth in full herein.

FIELD OF THE INVENTION

The present invention relates to methods for imaging an abnormality of vascular reactivity, for example, cerebrovascular reactivity (CVR), broadly defined as an abnormality in a vascular response relative to a control population, as evident from high resolution imaging.

BACKGROUND OF THE INVENTION

The measurement of cerebrovascular reactivity (CVR), whereby a strong vasoactive stimulus is applied to expose occult clinical limitations in regional cerebral blood flow (CBF) reactivity constitutes a cerebrovascular stress test. Quantitatively, CVR is defined as the change in CBF in response to a measurable stimulus. A surrogate high resolution measure of changes in CBF can be obtained by exploiting the Blood Oxygen Level Dependent (BOLD) effect of magnetic resonance imaging (MRI); and a measurable increase in the end-tidal (end-exhaled) partial pressure of $CO_2$ (PETCO$_2$) may be used as a surrogate measure for the true independent stimulus, the partial pressure of $CO_2$ in arterial blood (PaCO$_2$). CVR is can then optionally be defined as the percent change in BOLD signal (arbitrary units) per mmHg change in PaCO$_2$. CVR values can be color coded and superimposed, on the corresponding voxel on an anatomical scan to generate CVR maps. Of particular interest in the CVR maps are the detection of areas of paradoxical reductions in flow following the application of a vasodilatory stimulus, termed 'steal'. Steal has been shown to exist in deep white matter in healthy people [Mandell, 2008] as well as associated with pathology such as arteriovenous malformations [Fierstra, 2011], vasculitis [Han, 2008], steno-occlusive vascular disease [Han, 2011]; and associated with disease in the form of cortical thinning [Fierstra, 2010], cognitive decline [Balucani, 2012; Silvestrini, 2011], and enhanced risk of stroke [Silvestrini, 2000; Markus, 2001].

Whereas the presence of steal is highly specific for identifying compromised CVR, the absence of steal does not necessarily imply normal CVR. For example, CVR may be considerably reduced, but steal is absent if the stimulated demand fails to exceed its supply capacity. Alternatively, if the reduction of CVR is widespread and uniform, rather than localized, a differential in vasodilatory capacity between vascular territories may not exist and therefore, steal may not occur [Sobczyk 2014]. Steal may also not occur if compromised vessels maintain greater than some threshold vasodilatory reserve. Under these conditions, the absolute value of CVR may be less than 'normal' but the extent of reduction cannot be assessed unless the normal range of CVR is known for each anatomical location.

The range of CVR in healthy subjects is large and varies from region to region. Thus, even substantial reductions in CVR in one region will overlap with normal values in another resulting in difficulty in distinguishing reduced CVR due to pathophysiology from normally low CVR. Because the interpretation and assessment of CVR maps currently relies on subjective assessments, it is difficult to identify reduced CVR short of that causing 'steal'.

Currently however, the interpretation and assessment of CVR maps relies on a qualitative review of possible abnormalities, viewed as inhomogeneities in the CVR maps that appear to differ from the CVR maps of healthy individuals. Such qualitative comparisons require considerable experience for correct interpretation; areas where blunted CVR is present may be misinterpreted as healthy responses.

SUMMARY OF THE INVENTION

We describe a method of assessing the severity and distribution of an abnormality or reduction in a subject's vascular response to a vasoactive stimulus in at least one region of interest (ROI) of the subject's brain.

The vasoactive stimulus is in the form of at least one change in a subject's arterial partial pressure of carbon dioxide (each arterial partial termed a $PaCO_2^T$). Measured PetCO$_2$ values are used as a surrogate measure of the true stimulus.

The targeted $PaCO_2^T$(s) is maintained during the course of obtaining input of MR signals. Accordingly, the stimulus is standardized, allowing the severity and distribution of abnormal or reduced vascular response values to be assessed by using statistical scores such as z scores which reveal the severity and distribution of abnormal or reduced surrogate measures of blood flow as revealed by MRI.

According to one aspect, the invention is directed to method of assessing the severity and distribution of an abnormality or reduction in a subject's vascular response to a vasoactive stimulus in at least one region of interest (ROI) of the subject's brain.

An MRI scanner and a selected MR imaging protocol are used to generate for members of a group of control subjects, a set of vascular response signals representing a non-pathological vascular response to at least one change in the subject's arterial partial pressure of carbon dioxide (each arterial partial pressure of carbon dioxide a $PaCO_2^T$) in at least one common ROI of each control subject's brain.

It will be appreciated that the control group need not represent a non-pathological response since any type of status/criterion/parameter can be controlled for for the purposes evaluating a test subject.

The vascular response is quantifiable, from a surrogate measure of blood flow, on a voxel by voxel basis, with reference to the voxel coordinates, from MR signals corresponding respectively to each $PaCO_2^T$ in the form of a response value per voxel.

The control subject's respective voxel coordinates are co-registered to a standardized space based on a set of anatomic landmarks.

A measure of variability of the vascular response values are computed on a voxel by voxel basis. The vascular response values measure at least one of the amplitude of the vascular response and the time course of the vascular response.

For example, a mean and standard deviation of the vascular response values for voxels corresponding to the at least one ROI are computed to define, for the control group as a whole, a set of statistical values respectively associated with individual voxels corresponding to the ROI (an atlas).

The MR scanner and the selected MR imaging protocol are used to obtain MR signals per voxel corresponding to the surrogate measure of blood flow for each $PaCO_2^T$ for a test subject.

By scoring (e.g. as z values) the test subject's response values for individual voxels in the at least one ROI (each voxel co-registered to the standardized space based on the set of anatomic landmarks), relative to the respective computed statistical values e.g. means and standard deviations per corresponding voxel, the severity and distribution of the abnormal or reduced vascular response is revealed.

The method may be implemented using a MR scanner and a stand alone CPU or dedicated MR image processor.

The processor obtains input of the "abnormal voxel" (pre-defined or user defined via a user interface) coordinates and scores.

The processor may employ program code to define a new to ROI.

The processor may employ program code to compare the scores to a threshold value.

The processor may employ program code to compare the scores to scores associated with a disease.

According to another aspect, the invention is directed to an imaging system for detecting an abnormality in a subject's response to a vasoactive stimulus in at least one region of interest (ROI) of the subject's brain. The vascular response values may measure at least one of the amplitude and time course of the vascular response.

In one embodiment, the imaging system comprises an MR scanner configurable, using a pre-selected MR protocol, to capture spatially resolved MR signals corresponding to the subject's vasoactive response to a standardized cerebrovascular stimulus comprising at least one targeted change in the subject's arterial partial pressure of carbon dioxide (each arterial $PCO_2$ a $PaCO_2^T$). Optionally, at least one $PaCO_2^T$ is attained from an initial steady state $PaCO_2$ value. Optionally, the at least one change in $PaCO_2$ is at least one of a series of increments or decrements in the subject's arterial partial pressure of carbon dioxide.

The imaging system also comprises a computer programmed to obtain input of the MR signals and implement an algorithm for analyzing the MR signals with reference to a pre-determined surrogate measure of blood flow in the at least one ROI, the pre-determined surrogate measure of blood flow optionally quantifying at least one of the amplitude of the subject's vascular response and a time constant of the subject's vascular response to the at least one $PetCO_2^T$ (at least one change from a steady value or two targeted values) The algorithm includes program code for processing the MR signals with reference to the selected surrogate measure of blood flow for each $PetCO_2^T$ including computing a vasoactive response value per voxel, each voxel co-registered into a standardized space, and scoring the subject's vascular response values for respective individual voxels in the ROI, relative to statistical reference values, optionally using scores, for example z scores.

The imaging system optionally includes a user interface operable to initiate the aforesaid algorithm and optionally to map the scores back onto an anatomical representation of the standardized space to generate a statistical map of the subject's vascular response to a standardized cerebrovascular stimulus, wherein the probability that subject's vascular response to the standardized cerebrovascular stimulus is pathological is depicted, on a voxel by voxel basis, on the statistical map (e.g. a z map) for example using a color scheme wherein different colors are assigned to different scores such that each color pixel is mapped onto its anatomical 3 dimensional origin. The probability that the vascular response is part of the normal range may be represented by a z score, where high z scores represent lower probability that they are in the normal range and correspondingly higher probability of resulting from underlying pathology.

The reference values are a measure of the amount and variability of the vasoactive response and optionally comprise a mean and standard deviation of vascular response values per voxel for a corresponding ROI in a group of control subjects, the vascular response values generated using the pre-selected MR protocol for each same $PaCO_2^T$ and quantifying, on a voxel by voxel basis, the statistical scores e.g. the mean and standard deviation of the selected surrogate measure of blood flow (amplitude or tau or both). The vascular response values are generated from a set of MR signals corresponding to the control subjects' respective vascular responses per voxel, the respective voxel coordinates per subject co-registered to a standardized space based on a set of anatomic landmarks.

The MR scanner captures MR signals from the brain, as surrogates of brain blood flow, wherein the change in signal corresponds to the subject's vasoactive response to the stimulus. The stimulus is standardized with respect to strength preferably via induction of at least two levels of arterial partial pressure of carbon dioxide ($PaCO_2$), at least one of which is hypercapnic, or greater than the baseline resting level of the subject, and the level of which can be determined directly by arterial blood sampling or noninvasively by its surrogate, the end tidal, or end exhaled partial pressure of carbon dioxide.

For example, where the MR signals quantify the subject's vasoactive response to each of a series of targeted increments in the subject's end tidal partial pressure of carbon dioxide, each a $PetCO_2^T$, the reference values include a statistical summary of the control subjects' respective vascular response values to each $PetCO_2^T$.

Optionally, the images represent a change in the blood oxygen level dependent (BOLD) effect of a MR response to a targeted change in a subject's end tidal $PCO_2$ ($P_{ET}CO_2^T$).

Optionally, the images depict a change in the blood flow as measured by arterial spin labeling MR response to a targeted change in a subject's end tidal $PaCO_2$.

Optionally, the program code is operable on a dedicated image processor connected to or forming part of the MR scanner hardware. Alternatively, the MR signals are recorded in a file, optionally a file according to the DICOM standard and processed by a separate computer.

Optionally, the statistical scores are optionally further compared to threshold values per voxel associated with a particular disease, on a voxel by voxel basis.

The statistical scores e.g. z scores may be used to identify a new ROI, for example a smaller ROI within an ROI of the subject's brain that was of interest, a priori, in virtue of the pathology being assessed or in virtue of a prior, concurrent or later assessment. Optionally, the algorithm includes program code for identifying the new ROI.

In another aspect, the invention is directed to a computer program product comprising program code/instructions for executing the above-described algorithm, and optionally the reference values and/or program code for accessing the computer remotely to compare a subject's MR signals corresponding to the selected surrogate measure of blood flow with reference values and same targeted arterial partial pressures of carbon dioxide. Optionally, the computer program product comprises program code for producing a color coded statistical map and/or program code for identifying a new ROI.

In another aspect, the invention is directed to a non-transitory computer readable medium comprising program code for executing the above-described algorithm, and optionally the reference values and/or program code for accessing the computer remotely to compare a subject's MR signals corresponding to the selected surrogate measure of blood flow with reference values and same targeted arterial partial pressures of carbon dioxide. Optionally, the computer program product comprises program code for producing a color coded statistical map and/or program code for identifying a new ROI.

In one embodiment the reference scores are part of an atlas prepared for each a series of targeted increments in a subject's arterial partial pressure of carbon dioxide.

Thus, according to another aspect, the invention is directed to a method of characterizing an abnormality in a subject's vascular response to a vasoactive stimulus in at least one region of interest (ROI) of the subject's brain comprising the steps of:

a) using an MRI scanner and a selected MR imaging protocol to generate for members of a group of control subjects, a set of vascular response signals representing a non-pathological vascular response to at least one change in the subject's arterial partial pressure of carbon dioxide (each arterial partial pressure of carbon dioxide a $PaCO_2^T$) in at least one common ROI of each control subject's brain, wherein the vascular response is quantifiable, from a surrogate measure of blood flow, on a voxel by voxel basis, with reference to the voxel coordinates, from MR signals corresponding respectively to each $PaCO_2^T$ in the form of a response value per voxel;

b) co-registering the respective voxel coordinates in the at least one ROI for each control subject to a standardized space based on a set of anatomic landmarks;

c) computing, on a voxel by voxel basis, a mean and standard deviation of the vascular response values for voxels corresponding to the at least one ROI to define, for the control group as a whole, a set of statistical values respectively associated with individual voxels corresponding to the ROI (an atlas);

d) using the MR scanner and the selected MR imaging protocol to obtain MR signals per voxel corresponding to the surrogate measure of blood flow for each $PaCO_2^T$ for a test subject, by scoring the test subject's response values for individual voxels in the at least one ROI (each voxel co-registered to the standardized space based on the set of anatomic landmarks), relative to the respective computed means and standard deviations per corresponding voxel, as z values.

Optionally, the method further comprises the step of color-coding the z values and mapping the color-coded values back onto an anatomical representation of the standardized space to produce a z map. The invention is also directed to such z maps and their use as a diagnostic tool.

Optionally, the co-registered MR images are full brain images defining a substantially full set of potential ROIs.

Optionally, the standardized cerebrovascular stimulus is a vasodilatory stimulus.

Optionally, the vasodilatory stimulus is at least one targeted increase in the subject's end tidal PCO2, optionally from a steady state $PetCO_2$ or a previously targeted value.

Optionally, the stimulus is a series of increment or decrements in a subject's arterial partial pressure of carbon dioxide (a so-called ramp sequence).

Optionally, the reference values in an atlas are generated using a ramp sequence.

As described below, statistical maps such as z maps can be used to interpret interval differences and values for gain, phase and coherence emerging from a transfer function analysis.

Optionally, the images represent a change in a blood oxygen level dependent (BOLD) magnetic resonance imaging (MRI) response to a targeted increase in a subject's end tidal $PCO_2$ ($PetCO_2$), the vascular response values representing, for example, a change in BOLD MRI signal ($\Delta S$), in response to a standardized increase in the $PetCO_2$ (CVR=$\Delta S/\Delta PetCO_2$).

Optionally, the set of control subjects are selected on the basis that they report being free of neurological disease.

Optionally, the control subjects are matched for a parameter that is appropriate for the condition being examined in a patient. The term patient is used broadly to define a subject being tested with reference a selected control population.

Optionally, the set of control subjects are matched for at least one of age and gender.

According to one embodiment, the invention is directed to a method of assessing the severity and distribution of an abnormality or reduction in a subject's vascular response to a vasoactive stimulus in at least one region of interest (ROI) of the subject's brain, comprising the steps of:

a) using an MRI scanner and a selected MR imaging protocol to generate for members of a group of control subjects, a set of vascular response signals representing a control (e.g. non-pathological) vascular response to at least one change in the subject's arterial partial pressure of carbon dioxide (each arterial partial pressure of carbon dioxide a $PaCO_2^T$) in at least one common ROI of each control subject's brain, wherein the vascular response is quantifiable, from a surrogate measure of blood flow, on a voxel by voxel basis, with reference to the voxel coordinates, from MR signals corresponding respectively to each $PaCO_2^T$ in the form of a response value per voxel;

b) co-registering the control subject's respective voxel coordinates to a standardized space based on a set of anatomic landmarks;

c) computing, for the set of control subjects, on a voxel by voxel basis, at least one statistical value describing the quantity and variability of vascular response values associated with corresponding voxels of the standardized space to define at least for the region of interest, at least one statistical value per voxel in the ROI for the control group as a whole (an atlas);

d) using the MRI device and the selected imaging protocol to obtain MR signals per voxel corresponding to the surrogate measure of blood flow for each $PaCO_2^T$ for a test subject, by scoring the test subject's response values for individual voxels in the at least one ROI (each voxel co-registered to the standardized space based on the set of anatomic landmarks), relative to the at least statistical value per voxel computed in step c), wherein the scoring yields a score per voxel describing the manner in which the patient's vascular response values rank in comparison with the corresponding atlas values.

In one embodiment, the method excludes the MR scans (for one of or for both the test and control subjects) and optionally also excludes preparation of the reference value atlas from the MR signal data (DICOM), the method comprising, for example, the steps required to compute z scores, namely: (a) obtaining input of the test subject's vascular response values per voxel; (b) obtaining input of the statistical values per voxel (the reference values); and (c) computing the z values.

The reference values comprise statistical values, for example, a mean and standard deviation of respective control subject's vascular response values per voxel for a corresponding ROI in each member of the group of control subjects, the reference values and the test subject's vascular response values per voxel derived from MR signals obtained from an MR scanner using a pre-selected MR protocol and including respective voxel coordinates co-registered to a standardized space based on a set of anatomic landmarks; the vascular response values corresponding to and quantifying an individual subject's (control or test subject) vascular response to at least one change in the individual subject's arterial partial pressure of carbon dioxide (each arterial partial pressure of carbon dioxide a $PaCO_2^T$) in at least one common ROI of each individual subject's brain, wherein the vascular response is quantified, from a surrogate measure of blood flow, on a voxel by voxel basis, the MR signals quantifying at least one of the amplitude of the individual subject's vascular response and a time constant of the individual subject's vascular response to the each $PaCO_2^T$, wherein the scores e.g. z scores, identify the severity and distribution of an abnormality or reduction in the test subject's vascular response to the vasoactive stimulus.

After obtaining input of the test-subject's vascular response values corresponding to at least one region of interest (ROI) of the test subject's brain, obtaining input of reference values for each voxel in the ROI (an atlas) for a group of control subjects (e.g. by interrogating a database), and scoring the test subject's vascular response values for respective individual voxels in the ROI, relative to the corresponding reference values per voxel using the scores, the scores and voxel coordinates may be compared to a threshold value, for example to define the extent and distribution of an abnormality.

Optionally, the vascular response values are a measure of a delay in vascular response to the at least one change in the subject's arterial partial pressure of carbon dioxide, wherein at least one statistical value is determined for each respective voxel using a transfer function analysis. For example, a polynomial function may be computed to match the MR signals constituting the vascular response.

Optionally, the at least one statistical value is tau, a standardized transfer function analysis for all subjects optionally employing a mono-exponential dispersion function to generate an atlas of tau values.

Optionally, the atlas response values are rank ordered on a voxel by voxel basis. For example, the test subject response values per voxel are assigned a rank score following the rank order to generate a rank score map.

Optionally, a log transformation of the respective (voxel by voxel) vascular response values for the individual control subjects shows that the values are generally normally distributed. The individual control subject vascular response values and patient vascular response values are transformed, on a voxel by voxel basis, by taking the log of the values, and wherein a mean and SD of the control subjects respective vascular responses log transformed values is computed on a voxel by voxel basis to generate an atlas, and wherein the patient's respective vascular responses log transformed values are respectively scored with a z value.

Optionally, the method further comprises the step of color coding the scores and mapping the color-coded scores back onto an anatomical representation of the standardized space.

Optionally, the test subject and the control subjects are each scanned on one occasion to obtain a set of response values per voxel (A) and then each re-scanned at least once after an interval to obtain another set of response values per voxel (B). Optionally, a voxel mean and standard deviation with respect the quantum and variability of the respective differences (e.g. consistently A image values per voxel minus B image values per voxel, or consistently B image values minus A image values) between the test and re-test vascular response values for the control group of subjects, wherein the differences between the patient's test response and re-test response for respective voxels corresponding to the at least one ROI are scored, relative to the voxel means and standard deviations (optionally the means and standard deviation per voxel of the respective computed differences), using z values.

Thus, according to another aspect, the invention is directed to a method of assessing the severity and distribution of an abnormality or reduction in a subject's vascular response to a vasoactive stimulus, in at least one region of interest (ROI) of the subject's brain, comprising the steps of:

a) using an MRI scanner and a selected MR imaging protocol to generate for members of a group of control subjects, a first set (A) of vascular response signals representing a control (e.g. non-pathological) vascular response to at least one change in the subject's arterial partial pressure of carbon dioxide (each arterial partial pressure of carbon dioxide a $PaCO_2^T$) in at least one common ROI of each control subject's brain, wherein the vascular response is quantifiable, from a surrogate measure of blood flow, on a voxel by voxel basis, with reference to the voxel coordinates, from MR signals corresponding respectively to each $PaCO_2^T$ in the form of a response value per voxel;

b) re-testing each control subject at least once after an interval at each $PaCO_2^T$ using the MRI scanner and the selected MR imaging protocol to obtain at least one second set (B) of the vascular response signals representing at least one additional measurement of each control subject's (e.g. non-pathological) vascular response per voxel;

c) optionally, computing a value representing the difference between the respective test vascular response values and the re-test vascular response values for each individual control subject (consistently A image values minus B image values, or consistently B image value minus A image values), on a subject by subject and voxel by voxel basis, for voxels corresponding to the at least one ROI;

d) co-registering the control subject's respective voxel to a standardized space based on a set of anatomic landmarks;

e) computing for the control group as a whole, on a voxel by voxel basis, a statistical value describing the quantum and variability of the test and re-test vascular response values, optionally a statistical value describing the quantum and variability of the computed differences between the test and re-test vascular response values for individual respective voxels corresponding to the at least one ROI and assigning those values to the standardized space (atlas);

f) using the MR scanner and the selected MR imaging protocol to measure a test vascular response and at least one re-test vascular response obtained after an interval, for a subject in need of an assessment of a vascular response (a test subject), at each $PaCO_2^T$, by scoring the difference between the test subject's test vascular response values and re-test vascular response values for respective voxels corresponding to the at least one ROI against the control group variability in vascular response for the corresponding voxels.

In one embodiment, the method excludes the scans (test and control subjects) and optionally also excludes preparation of the reference value atlas, the method comprising the steps required to compute z scores, namely: (a) obtaining input of the A and B values per voxel (or at least the differences per voxel) for the test subject; (b) obtaining input of means and standard deviations per voxel of the differences between the A and B scores for the control group (the reference values); and computing the z values.

Optionally, the method further comprises the step of color-coding the z values and mapping the color-coded values back onto an anatomical representation of the standardized space to produce a z map.

Optionally, the co-registered voxel coordinates represent full brain images defining a substantially full set of potential ROIs.

Optionally, the standardized cerebrovascular stimulus is a vasodilatory stimulus. A vasoactive stimulus can optionally be a vasoconstrictive stimulus Optionally, the vasodilatory stimulus is at least one targeted increase in the subject's end tidal $PCO_2$ relative to an steady state baseline $PaCO_2$ or a previous targeted value which may optionally be an initial reduction in $PCO_2$.

Optionally, the images represent a change in a blood oxygen level dependent (BOLD) magnetic resonance imaging (MRI) response to a targeted increase in a subject's end tidal PCO2 ($P_{ET}CO_2$), the CVR response values optionally representing a change in BOLD MRI signal ($\Delta$ S), in response to a standardized increase in the $P_{ET}CO_2$ (CVR=$\Delta$ S/$\Delta$ $P_{ET}CO_2$).

Optionally, the set of control subjects are selected on the basis that they report being free of neurological disease.

Optionally, the set of control subjects are matched for at least one additional parameter that that defines a preferred subset of control subjects for the patient population for whom an assessment of an abnormality in vascular response is needed.

Optionally, the set of control subjects are matched for at least one of age and gender.

Optionally, the set of control subjects are selected on the basis that they report being non-smokers.

In another aspect, the invention is directed to a reference atlas of response values as generated in any manner defined above using a series of increments in a subject's arterial partial pressure of carbon dioxide as a stimulus, and to the use of such an atlas as a diagnostic tool in aiding of diagnosing a condition associated with an abnormal vascular response, for example a vascular disease or disease manifesting an abnormality in a vascular response. Optionally, the atlas is generated using a sequential gas delivery circuit (physical or virtual) wherein end tidal partial pressure of carbon dioxide are used as surrogates for targeted arterial partial pressures of carbon dioxide.

According to another aspect, the invention is directed to a neuro-imaging assessment method in aid of diagnosing at least one of the existence, location, deterioration and amelioration of a brain disorder associated with abnormal vascular reactivity (i.e. any abnormal vascular response including an abnormality in the amplitude and/or time course of the response), for example a cerebrovascular disorder.

The neuro-imaging assessment protocol of the present invention, including any permutations of the steps defined above or below, enables images to be produced from which such diagnostic assessments may be carried out and/or confirmed. According to one embodiment the invention, the organ is brain and the invention provides a novel cerebrovascular reactivity assessment protocol for producing a reference atlas, for example an atlas of non-pathological cerebrovascular reactivity.

Accordingly in a further embodiment, the invention provides for a method and for the use such an atlas of non-pathological cerebrovascular reactivity to produce brain imaging results e.g. neuro-imaging results from which a subject in need of assessment of abnormal cerebrovascular reactivity can be assessed for the abnormality. The method optionally comprises producing a reference atlas and comparing voxel by voxel test vascular response value of a patient to the corresponding reference atlas value by scoring those values, preferably in a manner that accounts for relative departure of the test value from a quantity describing a characteristic value (e.g. mean/SD for normal distributions of value or normal distributions of log values) such as to account for the variability or distribution of the control values.

According to another aspect the invention is directed to a diagnostic tools in the form of a neuro-image and other visual depictions such as graphs derived from such images that incorporate statistical transformations of MR signals generated in response to at least one targeted change in a subject end-tidal $PCO_2$. According to one embodiment the invention is directed to a cerebrovascular reactivity response map e.g. in the form a z map, tau z map or ID z map as described herein.

For example, according to one embodiment the organ is brain and the invention is directed to a diagnostic tool comprising color-coded z values mapped onto an anatomical representation of a standardized 3D map of at least one region of interest (ROI) of the brain, the z values and 3D map characterized in that a standardized set of MR imaging protocols are employed to generate for members of a group of control subjects, a set of CVR response signals depicting a non-pathological CVR response, in at least one common ROI of each control subject's brain, wherein the CVR response is a reaction to a standardized vasoactive stimulus, and wherein the CVR response is quantifiable from images corresponding to the response signals, on a voxel-by-voxel basis, in the form of CVR response value per voxel; and wherein b) a standardized algorithm is used to co-register the respective control subject images to a standardized space based on a set of anatomic landmarks;

c) a computation, for the set of control subjects, on a voxel by voxel basis, of a mean and standard deviation of the CVR response values for voxels corresponding to the at least one ROI is used;

d) the MR scanner and the standardized set of MR imaging protocols is used to measure a CVR response for a subject in need of an assessment of an abnormality in CVR, employing the standardized vasoactive stimulus by scoring the respective responses for individual voxels in the at least one ROI, relative to the computed mean and standard deviation, using z values.

Optionally, z values can be generated for test subjects that are based on a measurement of a plurality of CVR test values, on a voxel by voxel basis, for each respective control subject. Multiple CVR values per control subject are obtained from a plurality of imaging tests generated using a standardized stimulus and therefore reflect expected test/re-test variability in CVR measurements. The successive tests are preferably conducted on different days and optionally at different times of day, such that the plurality of variant values reflect primarily the inevitable variations corresponding to normal variations in physiology and in the technology (even despite using a single scanner), over time. The different values may also reflect in minor part differences due to other categories influences (e.g. unidentified sources of small variation or, identifiable sources of small variation of the type not generally subject to practical control).

The standard CVR atlas may reflect this retest values in the means and standard deviation per voxel. Alternative the probative value of such re-test values can be accentuated by generating a specialized reference atlas (an Interval Difference atlas) in which the control group means and standard deviations are calculated with respect to intra-subject differences e.g. say between the two test values for a subject which are subtracted from one another. The intra-subject test/re-test variability, however quantified or accounted for, both from an intra-control subject perspective and across a group of control subjects, is important for assessing a patient's change in CVR per voxel against a backdrop of normal re-test variability.

These so-called Interval Difference (ID) variations may be used to compute ID z values for a given control or diseased subject, and for creating for the group of subjects, an atlas of test-retest value differences, on a voxel by voxel basis. This enables an attribution of the statistical probability that changes in CVR to true interval change in pathophysiology. Optionally resulting ID-z values may be as reference maps to monitor progression of the disease over time or responses to treatment.

Optionally, the standardized cerebrovascular stimulus is a vasodilatory stimulus.

Optionally, the method is used in aid of diagnosing a neurological disorder

Optionally, the vasodilatory stimulus is a surrogate measure of the subject's arterial $PCO_2$ ($PetCO_2$), the surrogate measure optionally an end tidal partial pressure of carbon dioxide measured on a breath by breath basis. The stimulus is preferably controlled by targeting at least one increase (relative to a subject's baseline steady state value or a previously targeted value), in a subject's end tidal $PCO_2$.

As described herein, in any of the methods the standardized stimulus optionally provides for a subjects baseline $PetCO_2$ to be increased to a targeted value and returned to baseline, and optionally increased again to the same targeted value. Variations on such standardized protocols would be apparent to those skilled in the art of manipulating arterial blood gases.

Several surrogate measures of cerebral blood flow (CBF) are known to persons skilled in the art.

Optionally, the images represent a change in a Blood Oxygen Level Dependent (BOLD) magnetic resonance imaging (MRI) response to a targeted increase in a subject's end tidal $PCO_2$.

Optionally, the images depict a change in the blood flow as measured by arterial spin labeling MR response to a targeted change in a subject's end tidal $PaCO_2$.

The control subjects are preferably free of neurological disease and optionally also non-smokers.

Optionally, the control subjects are age and/or gender matched.

The subjects can be matched with respect to a wide variety of parameters including underlying disease, the use or non-use of certain medications etc.

The z maps or ID standardized z values are optionally employed for the detection of areas of paradoxical reductions in blood flow following the application of the vasodilatory stimulus ('steal'). In the same connection, parallel increases in blood flow elsewhere may also be indicative of an abnormality in a vascular bed.

Optionally, for non-parametric data one can rank order the voxel value in the reference atlas and then score the test voxel in terms of rank. Also, data can be transformed by taking the log of a measure and tested for normal distribution. If the logs are normally distributed, then the mean and SD of the logs are computed. The test voxel is then also transformed to log value and then scored with a z value.

In a further general aspect, the invention is directed to a method of using blood flow correlated high resolution imaging signals for characterizing an abnormality in a vascular response to a standardized vasoactive stimulus in at least one region of interest (ROI) in an organ, the method comprising the steps of:

a) using an high resolution imaging device and a standardized set of imaging protocols to generate, for respective members of a group of control subjects, a vascular response signal depicting, for each voxel corresponding to the at least one ROI, a control group member's vascular response to a standardized vasoactive stimulus, wherein the vascular response for the ROI for each control group member is quantifiable from images corresponding to the respective individual voxel response signals;

b) using a standardized algorithm to co-register respective control subject images to a standardized space based on a set of anatomic landmarks;

c) computing, for the co-registered set of control subject images, on a voxel by voxel basis, at least one statistical value describing the quantity and variability of vascular response values associated with corresponding voxels of the standardized space to define at least for the region of interest, at set of statistical value respectively associated with individual voxels corresponding to the ROI for the control group as a whole (an atlas);

d) using the high resolution imaging device and the standardized set of imaging protocols to measure a vascular response for a subject in need of a comparative vascular response assessment (patient), employing the standardized vasoactive stimulus by statistically scoring the patient's respective vascular responses values for each individual voxel relative to corresponding values in the atlas, to generate for each voxel at least one score describing how the patient's vascular response values rank in comparison with the corresponding atlas values such that the quantum and variability of the individual control group member vascular response values is taken into account in the score.

Optionally, the method further comprises the step of color-coding the scores and mapping the color-coded scores back onto an anatomical representation of the standardized space to produce a vascular response map of the at least on ROI.

Optionally, the scores are z-scores and wherein the map is a z-map.

Optionally, the organ is brain.

Optionally, the high resolution imaging device is an MRI device, wherein the co-registered images are magnetic resonance images.

Optionally, the co-registered MR images are full brain images defining a substantially full set of potential ROIs.

Optionally, the standardized cerebrovascular stimulus is a vasodilatory stimulus.

Optionally, the vasodilatory stimulus is at least one targeted increase in the subject's end tidal $PCO_2$ from a steady state PetCO2.

Optionally, the images correspond to signals representing a change in a blood oxygen level dependent (BOLD) MRI response to a targeted increase in a subject's end tidal $PCO_2$ ($P_{ET}CO_2$), the vascular response values optionally representing a change in BOLD MRI signal ($\Delta$ S), in response to a standardized increase in the $P_{ET}CO_2$ ($\Delta$ S/$\Delta$ $P_{ET}CO_2$). As mentioned above, ASL may be used in to measure a change in blood flow in response to a standardized $PCO_2$ stimulus.

Optionally, the vascular response values are a measure of a delay in the vascular response to the standardized vasoactive stimulus, the at least one statistical value determined for each respective voxel using a standardized transfer function analysis wherein a polynomial function is computed to match the vascular response signal data.

Optionally, the at least one statistical value is tau, the standardized transfer function analysis employing a monoexponential dispersion function (exemplified herein) to generate an atlas of tau values.

Optionally, the atlas response values are rank ordered on a voxel by voxel basis and wherein the corresponding patient response values are assigned a rank score following the rank order to generate a rank score map.

Optionally, a log transformation of the respective (voxel by voxel) vascular response values for the individual control subjects shows that the values are generally normally distributed and wherein the individual control subject vascular response values and patient vascular response values are transformed, on a voxel by voxel basis, by taking the log of the values, and wherein a mean and SD of the control subjects respective vascular responses log transformed values is computed on a voxel by voxel basis to generate an atlas, and wherein the patient's respective vascular responses log-transformed values are respectively scored with a z value.

Optionally, each of the members of the group of control subjects are selected to represent healthy individuals exhibiting a non-pathological vascular response to the standardized vasoactive stimulus in the at least one ROI. Alternatively, the control group can be represented by any number of different criteria.

According to another aspect, the invention is directed to a neuro-imaging assessment method in aid of diagnosing at least one of the existence, location, deterioration and amelioration of a brain disorder associated with abnormal vascular reactivity, for example a cerebrovascular disorder.

The neuro-imaging assessment protocol of the present invention, including any permutations of the steps defined above, enables images to be produced from which such diagnostic assessments may be carried out and/or confirmed. According to one embodiment the invention provides a novel cerebrovascular reactivity assessment protocol for producing an atlas of non-pathological cerebrovascular reactivity. Accordingly, in a further embodiment, the invention provides a method of using such an atlas of non-pathological cerebrovascular reactivity to produce neuro-imaging results from which a subject in need of assessment of abnormal cerebrovascular reactivity can be assessed for the abnormality.

According to another aspect the invention is directed to a diagnostic tool in the form of a neuro-image and other visual depictions such as graphs derived from such images that incorporate statistical values derived from MR signals generated in response to at least one targeted change in a subject's end-tidal $PCO_2$.

According to one embodiment the invention is directed to a cerebrovascular reactivity response map in the form a z map or ID z map, or tau z map as described herein.

For example, according to one embodiment the invention is directed to a diagnostic tool comprising color-coded z values mapped onto an anatomical representation of a standardized 3D map of at least one region of interest (ROI) of an organ e.g. brain, the z values and 3D map characterized in that a standardized set of imaging protocols are employed to generate for members of a group of control subjects, a set of vascular response signals depicting a non-pathological CVR response, in at least one common ROI of each control subject's organ of interest, wherein the vascular response is a reaction to a standardized vasoactive stimulus, and wherein the vascular response is quantifiable from images corresponding to the response signals, on a voxel-by-voxel basis, in the form of vascular response value per voxel;

b) a standardized algorithm is used to co-register the respective control subject images to a standardized space based on a set of anatomic landmarks;

c) a computation, for the set of control subjects, on a voxel by voxel basis, of a statistical value describing the quantity and variability of vascular response values associated with corresponding voxels of the standardized space, optionally a mean and standard deviation of the vascular response values for voxels corresponding to the at least one ROI is used;

d) the MR scanner and the standardized set of MR imaging protocols is used to measure a CVR response for a subject in need of an assessment of an abnormality in CVR, employing the standardized vasoactive stimulus by scoring the respective responses for individual voxels in the at least one ROI, relative to the e.g. computed mean and standard deviation, using e.g. z values.

According to another aspect the invention is directed a method of assessing the severity and distribution of an abnormality or reduction in a test subject's vascular response to a vasoactive stimulus in at least one region of interest (ROI) of the subject's brain, comprising the steps of:

(a) obtaining input of a test-subject's vascular response values per voxel corresponding to at least one region of interest (ROI) of the test subject's brain;

(b) obtaining input of reference values for at least each voxel in the ROI (an atlas) for a group of control subjects; and (c) scoring the test subject's vascular response values for respective individual voxels in the ROI, relative to the corresponding reference values per voxel using z scores;

wherein the reference values comprise a mean and standard deviation of respective control subject's vascular response values per voxel for a corresponding ROI in the group of control subjects, the reference values and the test subject's vascular response values per voxel derived from MR signals obtained from an MR scanner using a pre-selected MR protocol and including respective voxel coordinates co-registered to a standardized space based on a set of anatomic landmarks; the vascular response values corresponding to and quantifying an individual subject's (control or test subject) vascular response to at least one change in the individual subject's arterial partial pressure of carbon dioxide (each arterial partial pressure of carbon dioxide a $PaCO_2^T$) in at least one common ROI of each individual subject's brain, wherein the vascular response is quantified, from a surrogate measure of blood flow, on a voxel by voxel basis, the MR signals quantifying at least one of the amplitude of the individual subject's vascular response and a time constant of the individual subject's vascular response to the each $PaCO_2^T$.

BRIEF DESCRIPTION OF THE DRAWINGS

FIG. 1 is a series of axial slices for a normal cohort atlas displaying the spatial distribution of (A) mean CVR values coloured according to the scale shown on the right in % BOLD change/mmHg $P_{ET}CO_2$ change and (B) coefficient of variation (CV) values with colour scale on right in percent.

FIG. 3 illustrates the extent of expected high statistical abnormality, as a result of physiologic, technical, and anatomical variation in the subject as well as errors in matching of voxels during co-registration.

FIGS. 6A and 6B (Table 2) provide additional information and commentary for each subject. (Dx=diagnosis; MRA=magnetic resonance angiogram).

FIGS. 6A and 6B show a table (Table 2) providing additional information about the patients for whom magnetic resonance angiograms, CVR maps and corresponding z maps are provided in FIGS. 4 and 5 (Abbreviations: ACA, anterior cerebral artery; EC-IC, external carotid to internal carotid; GM, gray matter; Hx, History; ICA, internal carotid artery; L, Left; R right; MCA, middle cerebral artery; MM, Moyamoya; PCA, posterior cerebral artery; SD, standard deviation; TIA, transient ischemic attack; VA, vertebral artery; WM, white matter)

FIG. 7 is summary table (Table 3) comparing CVR maps and z-maps.

The distribution of changes in both positive and negative directions consistent with the history, and the magnitude of voxelwise divergence in interval differences from the sample ID atlas, establish that these changes were not due to technical or physiologic variability.

FIG. 12 is a Table describing the distribution of age and sex of the cohort of 46 control subjects.

Figure 13:
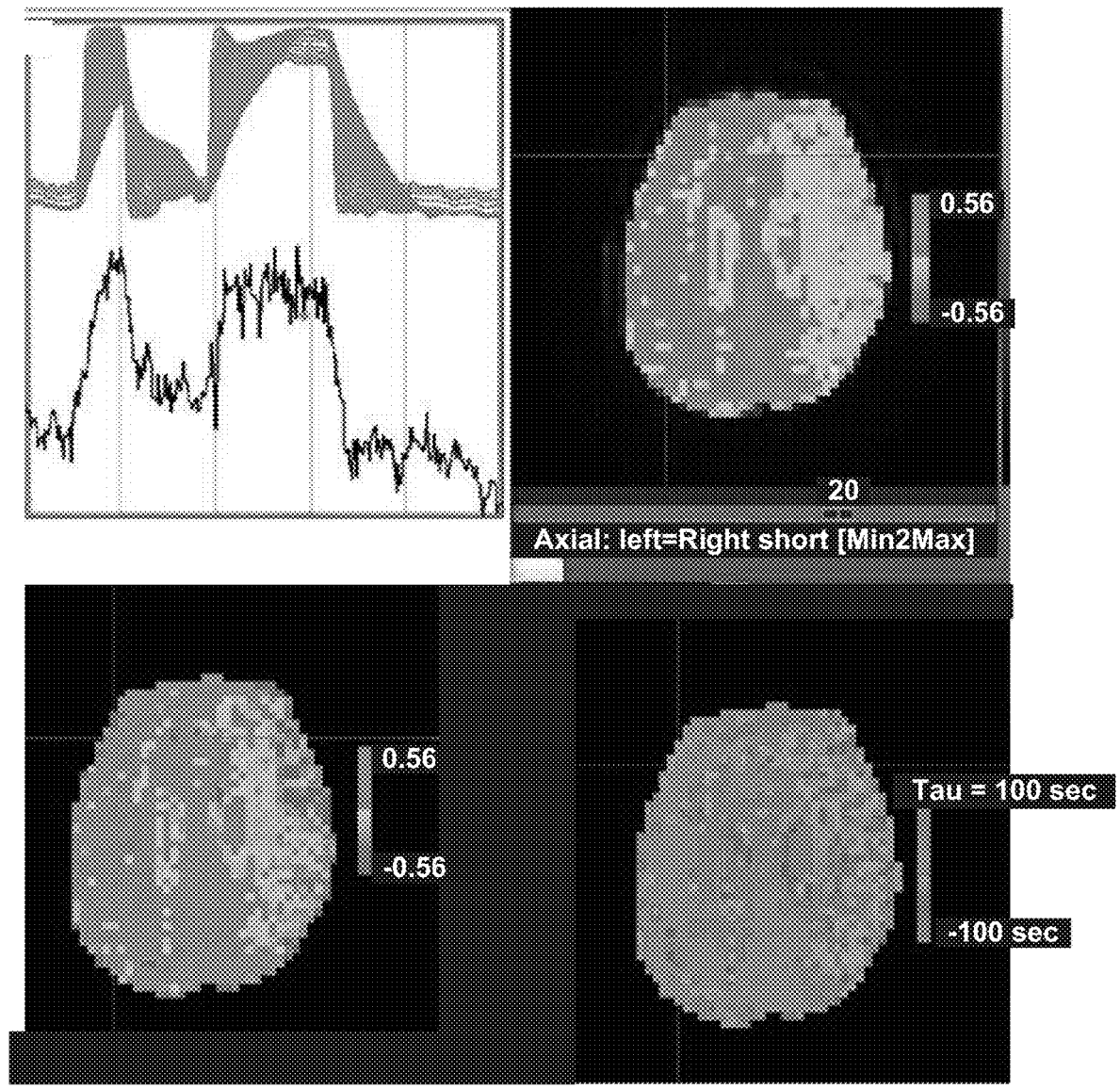

FIG. 13 presents in an upper left panel a series of deconvolved input signals-$PETCO_2$ (red lines) to match BOLD signal (black line) in one voxel (crosshairs) from which τ is calculated. The upper right panel is a CVR map. Lower left panel shows the amplitude of response as calculated from the matched deconvolved function. Lower right panel is the T map.

Figure 14:
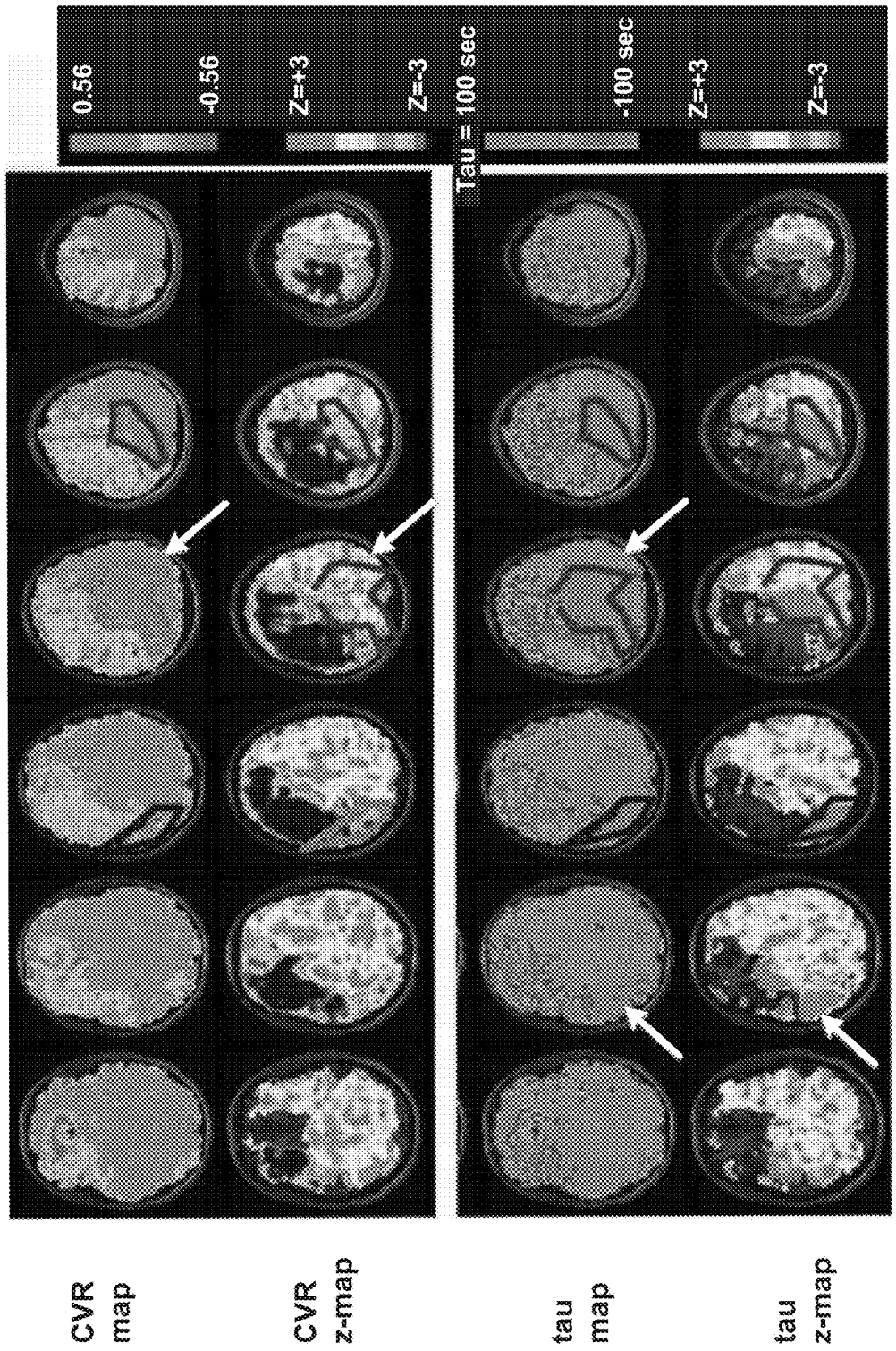

FIG. 14 presents CVR and tau maps and their respective z maps in a patient with right carotid artery stenosis. FIG. 14 shows an abnormal time response (tau and tau z values) in areas with normal or mildly abnormal CVR amplitude and z values (outlined, arrows).

Figure 15:
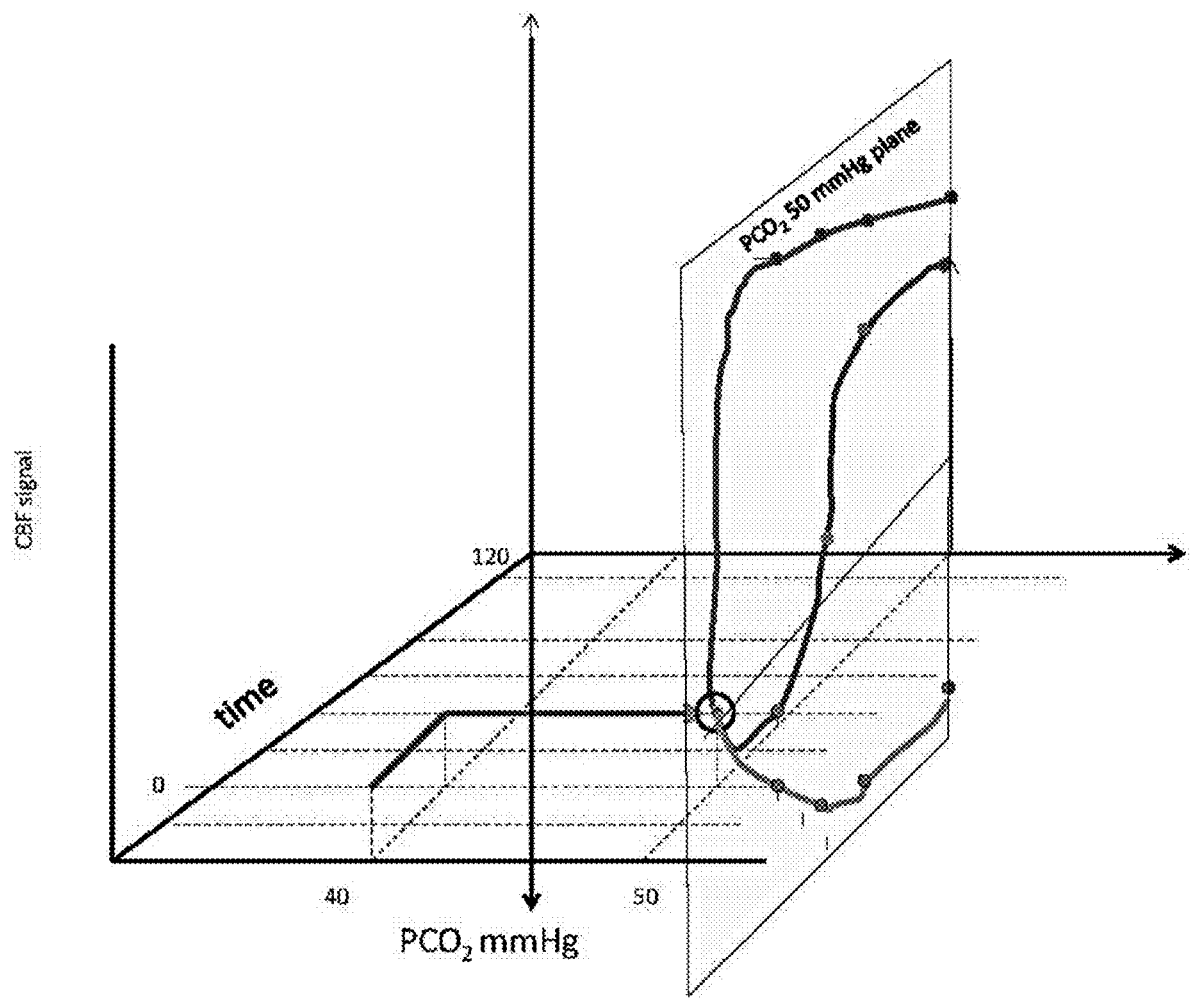

FIG. 15 is a graph illustrating a change of amplitude of a BOLD signal (CBF signal) (Y axis) as a function of $PCO_2$ in mmHg (X axis) and time (z axis) for robust (blue), dampened (red) and paradoxical (orange) responses.

FIGS. 16A-E provide illustrations characterizing the use of transfer function analysis to label each voxel as per gain and phase lag.

Co-registration of such maps for a reference cohort (sometimes described herein as a healthy or normal cohort) is accomplished as described below.

Means and SD are computed and then a z map is generated for our test subject of gain and lag phase. Theoretically, these values should correspond to CVR and T respectively.

The approach as illustrated in FIG. 16A yields three interpretable parameters that describe the magnitude with which CBF changes are driven by arterial pressure $PCO_2$ (gain) as well as the timing (phase) and linearity (coherence) of the relationship (Tzeng et al 2012).

Figure 16B:
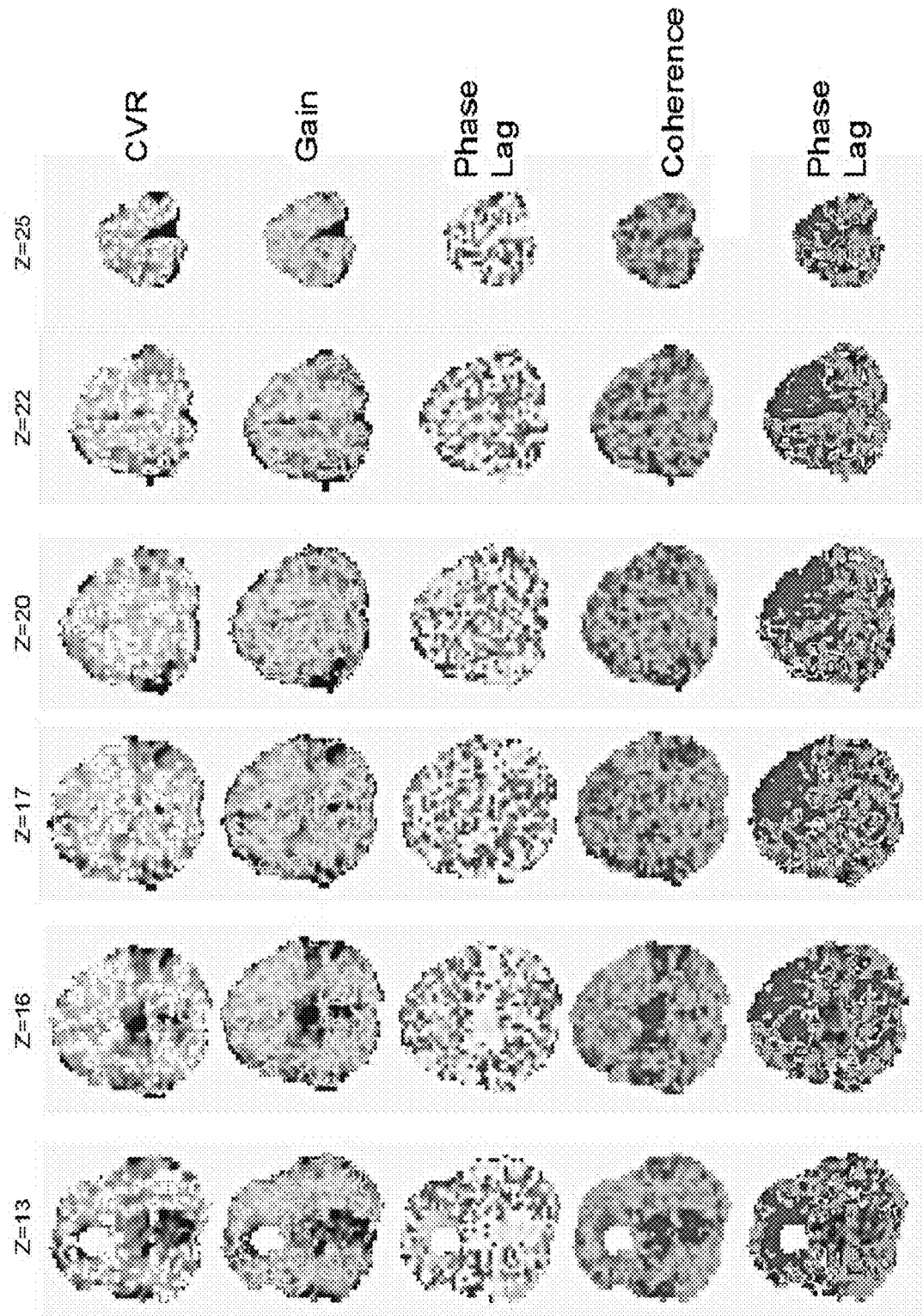
Figure 16C:
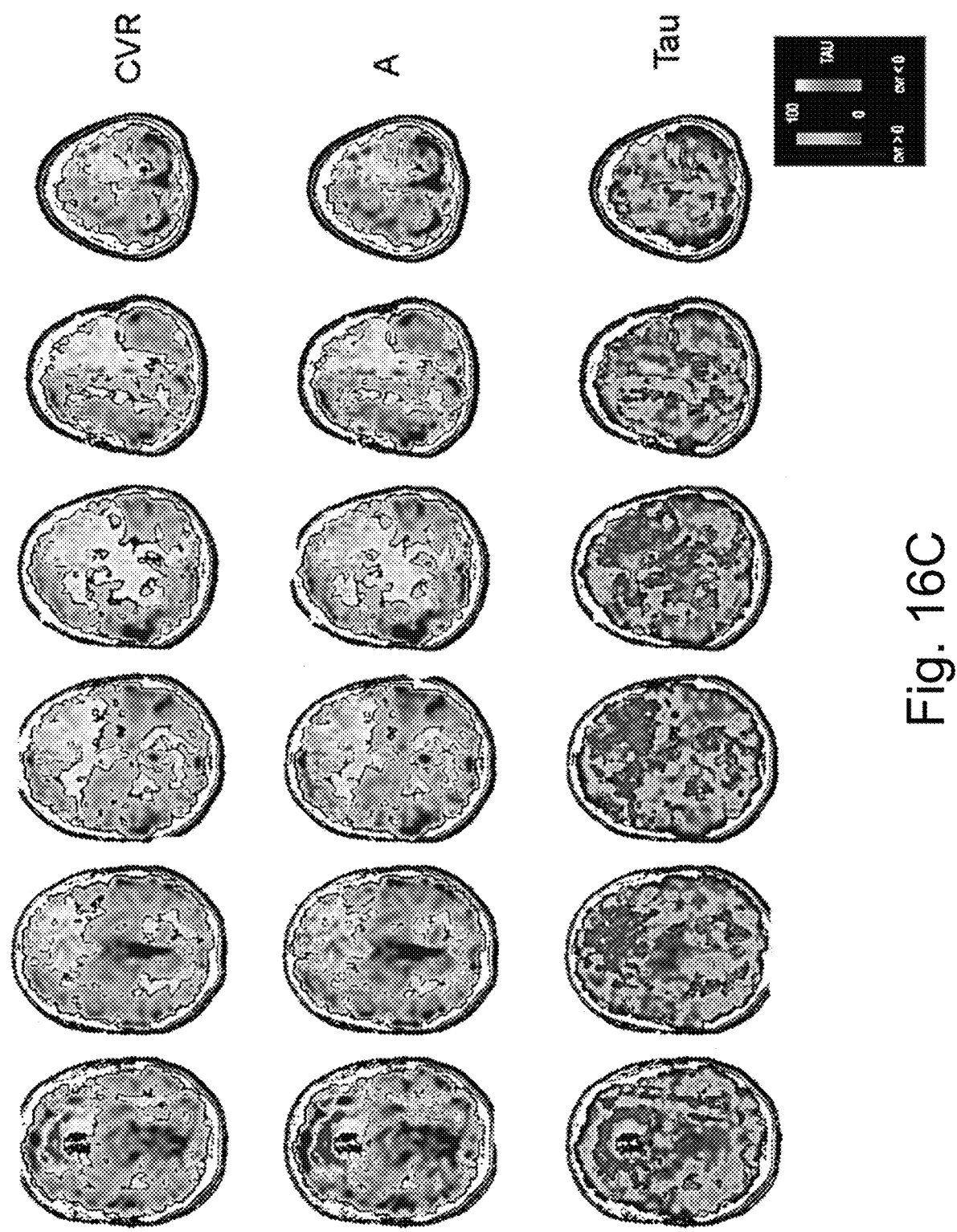
Figure 16D:
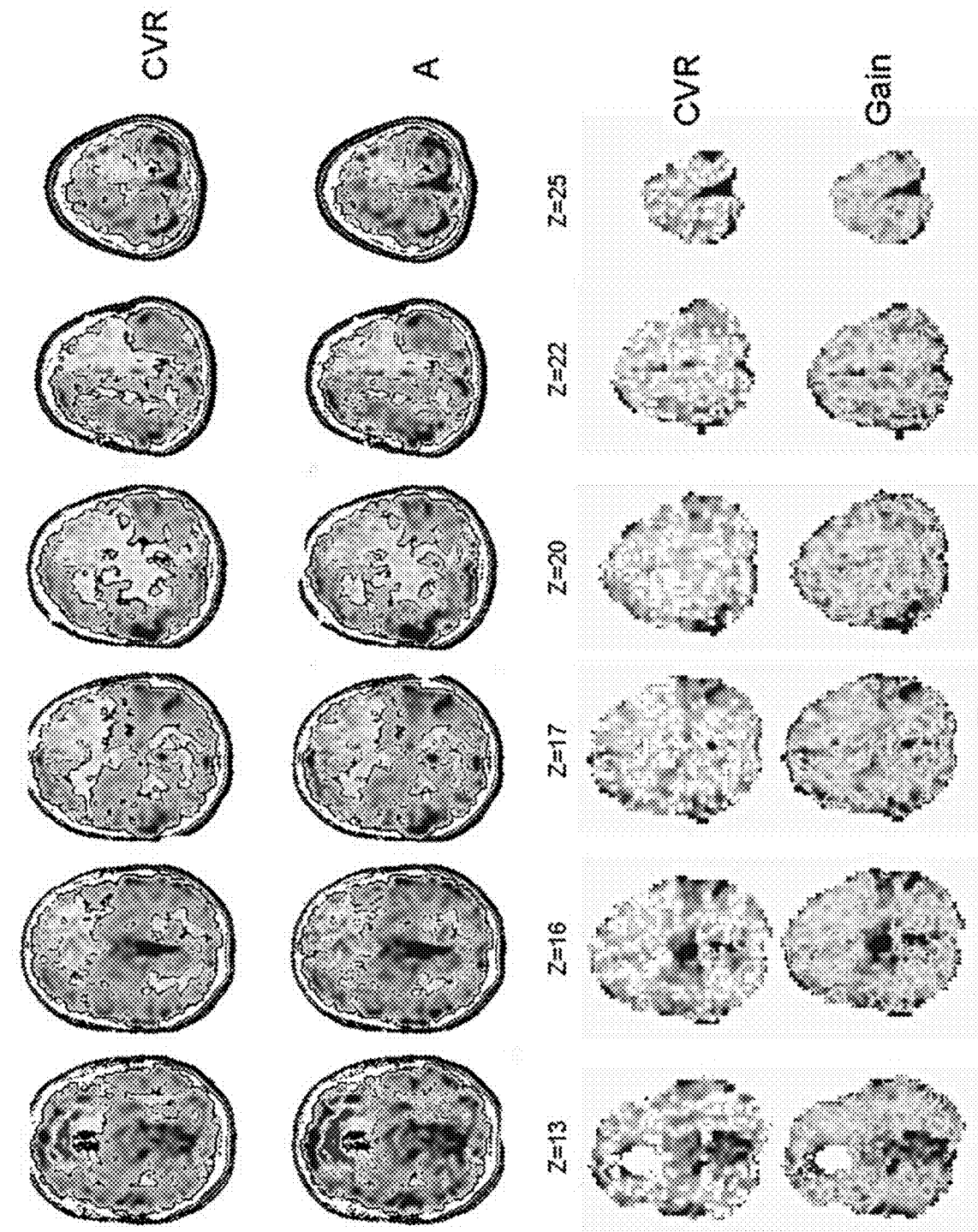
Figure 16E:
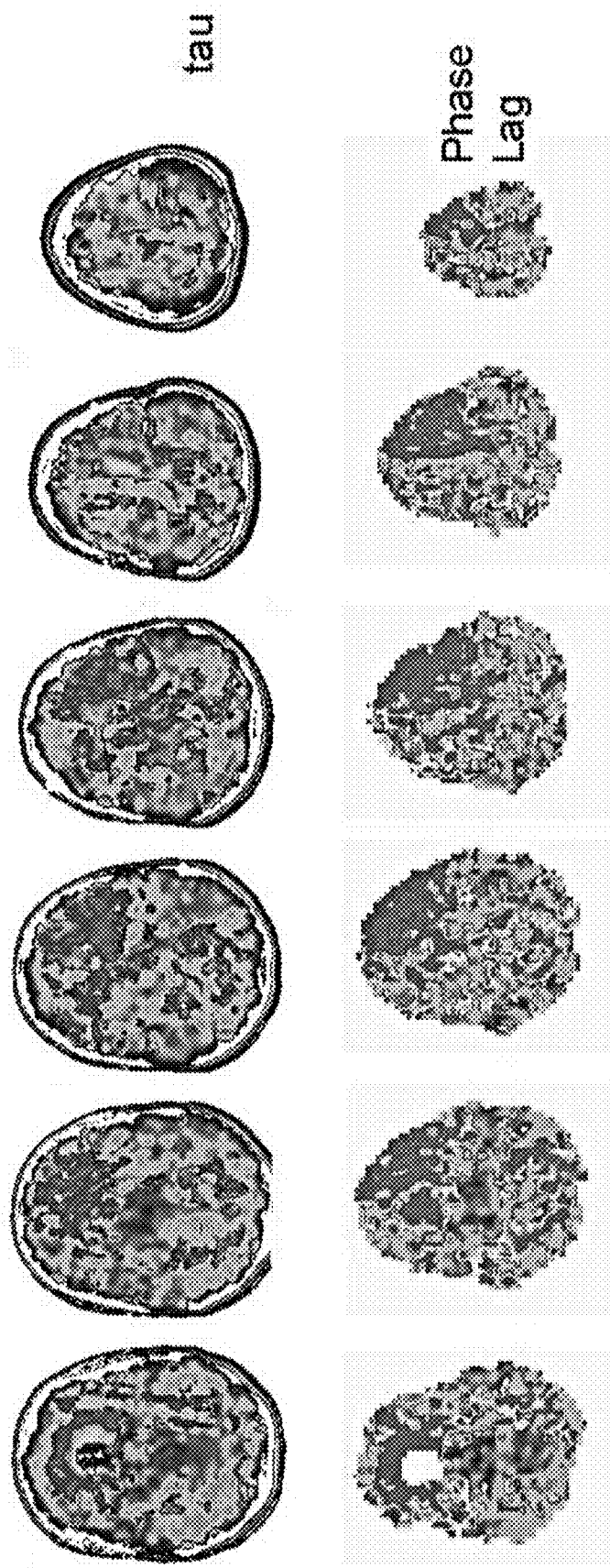

FIGS. 16B-16D images show that indeed they look very similar (compare CVR line to Gain line in FIG. 16B; and phase lag line slide 16B to T line in FIG. 16C. FIG. 16D compares images of amplitude from CVR amplitude measured (first line), amplitude calculated from T dispersion (second line), and gain using FTA (fourth line).

Figure 17A:
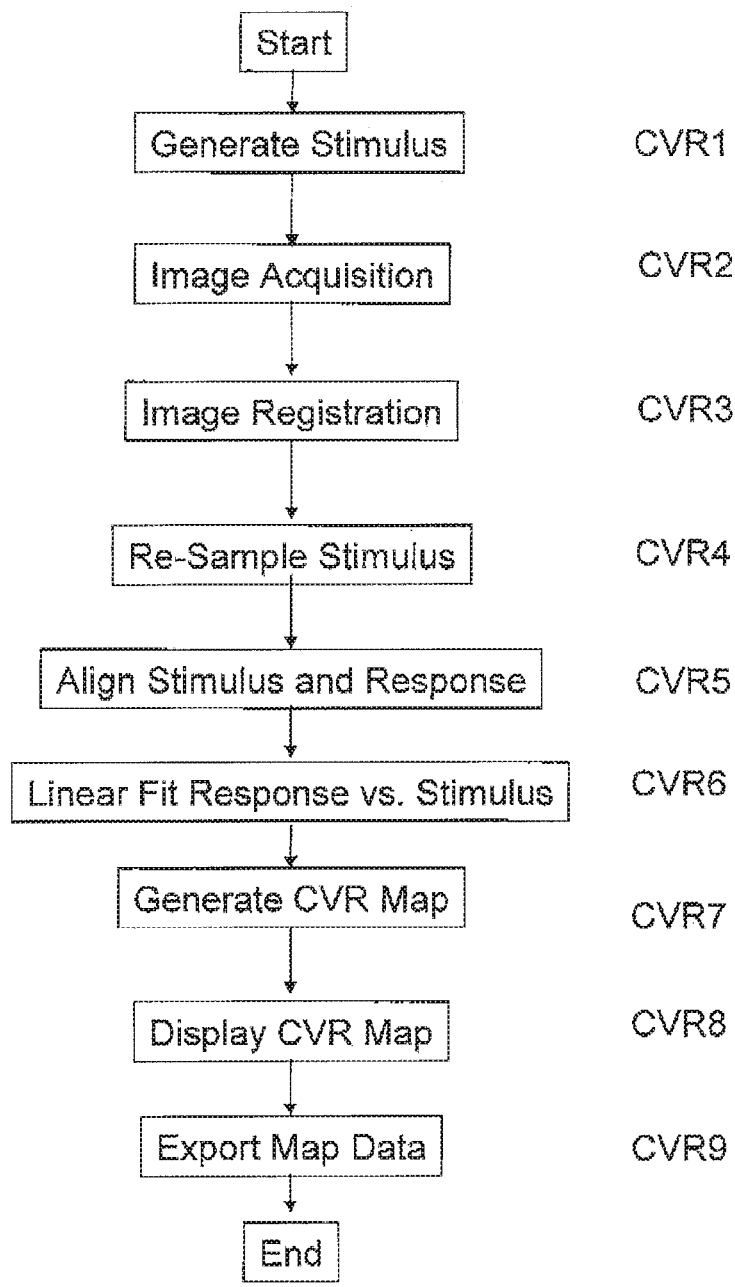

FIG. 17a is a flow chart showing a series of steps useful for producing vascular response data for a subject (control or patient) according to an embodiment of the invention.

FIG. 17b is table describing the nature and function of each step presented in FIG. 17a.

Figure 18A:
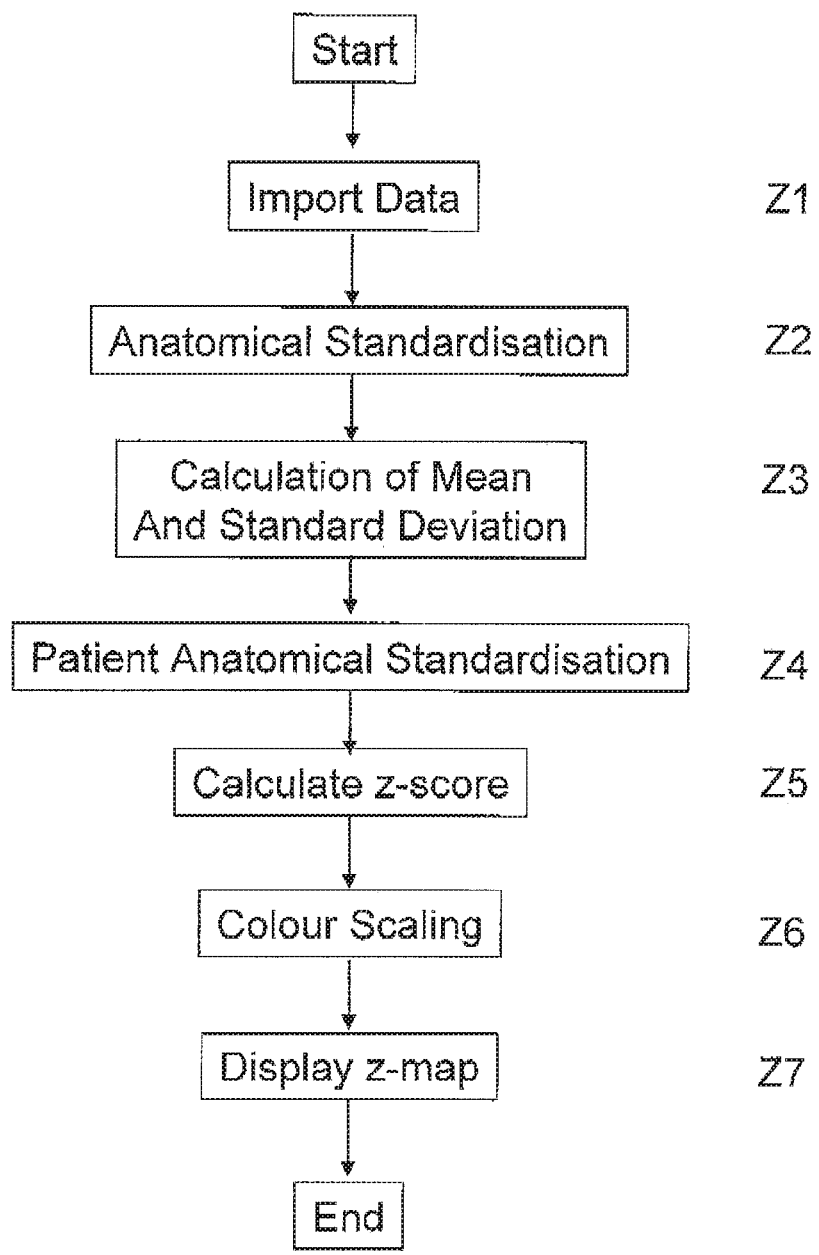

FIG. 18a is a flow chart showing a series of steps useful for producing z maps for a subject according to an embodiment of the invention. These z-map generation steps may applied to CVR, to amplitude, tau, gain, phase, coherence, interval differences etc.

FIG. 18b is table describing the nature and function of each step presented in FIG. 18a.

Figure 19A:
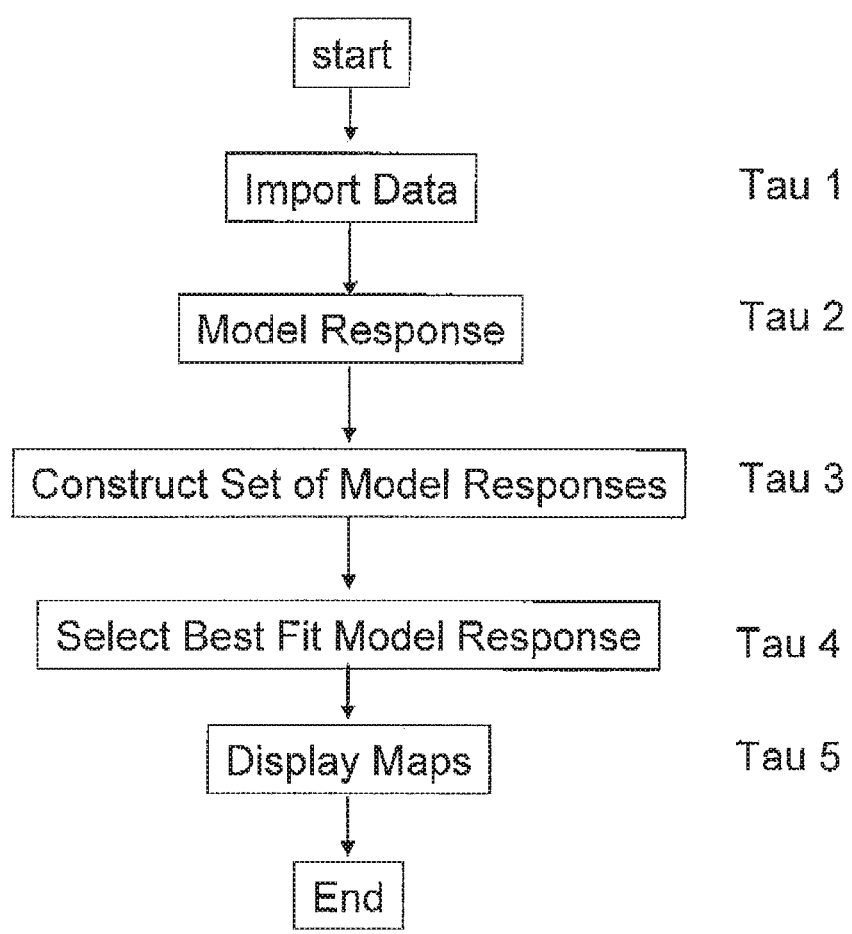

FIG. 19a is a flow chart showing a series of steps useful for producing tau response values per voxel in at least one ROI for a subject according to an embodiment of the invention.

FIG. 19b is table describing the nature and function of each step presented in FIG. 19a.

Figure 20A:
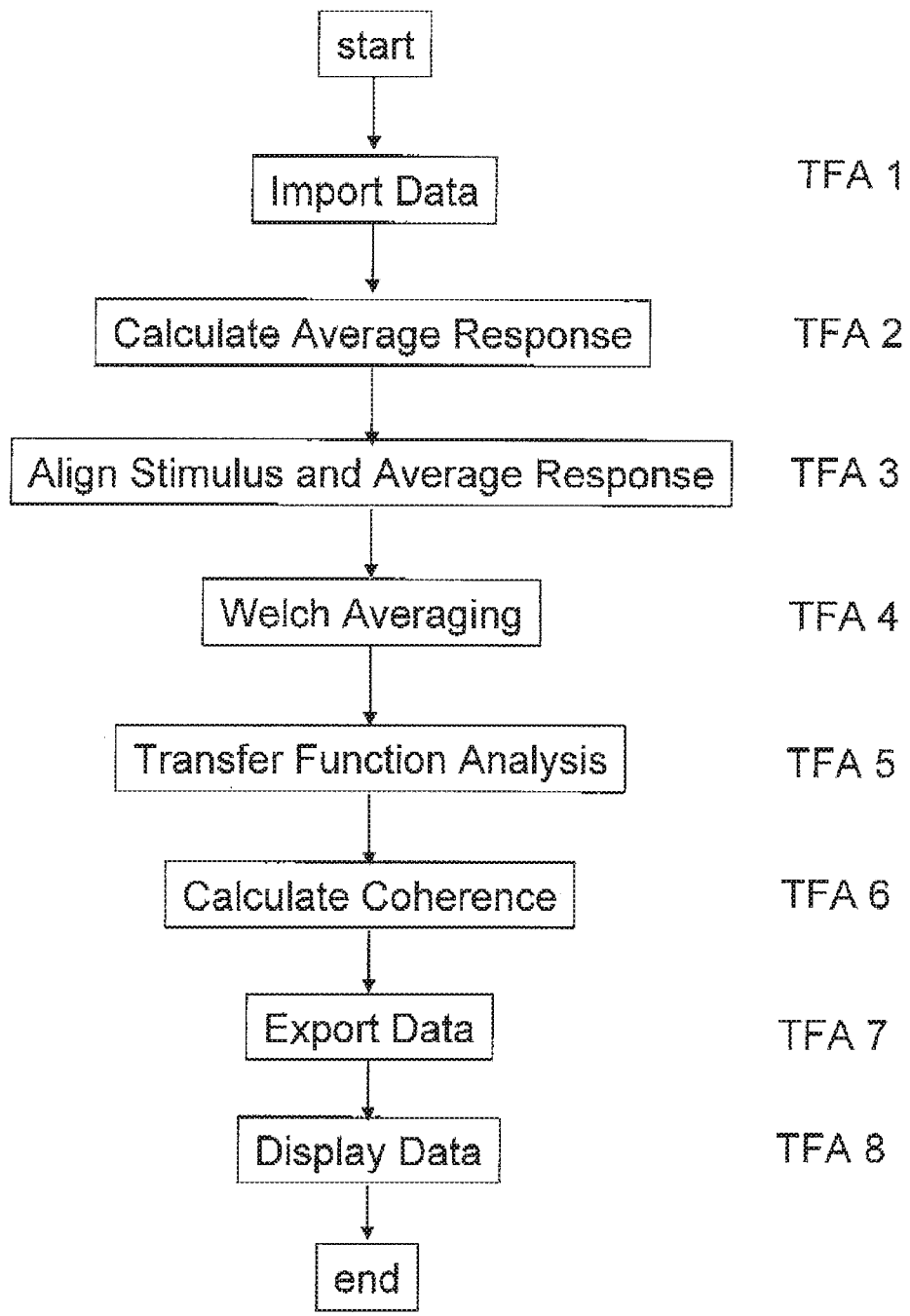

FIG. 20a is a flow chart showing a series of steps useful for conducting a transfer function analysis for a subject according to an embodiment of the invention.

FIG. 20b is table describing the nature and function of each step presented in FIG. 20a.

Figure 21A:
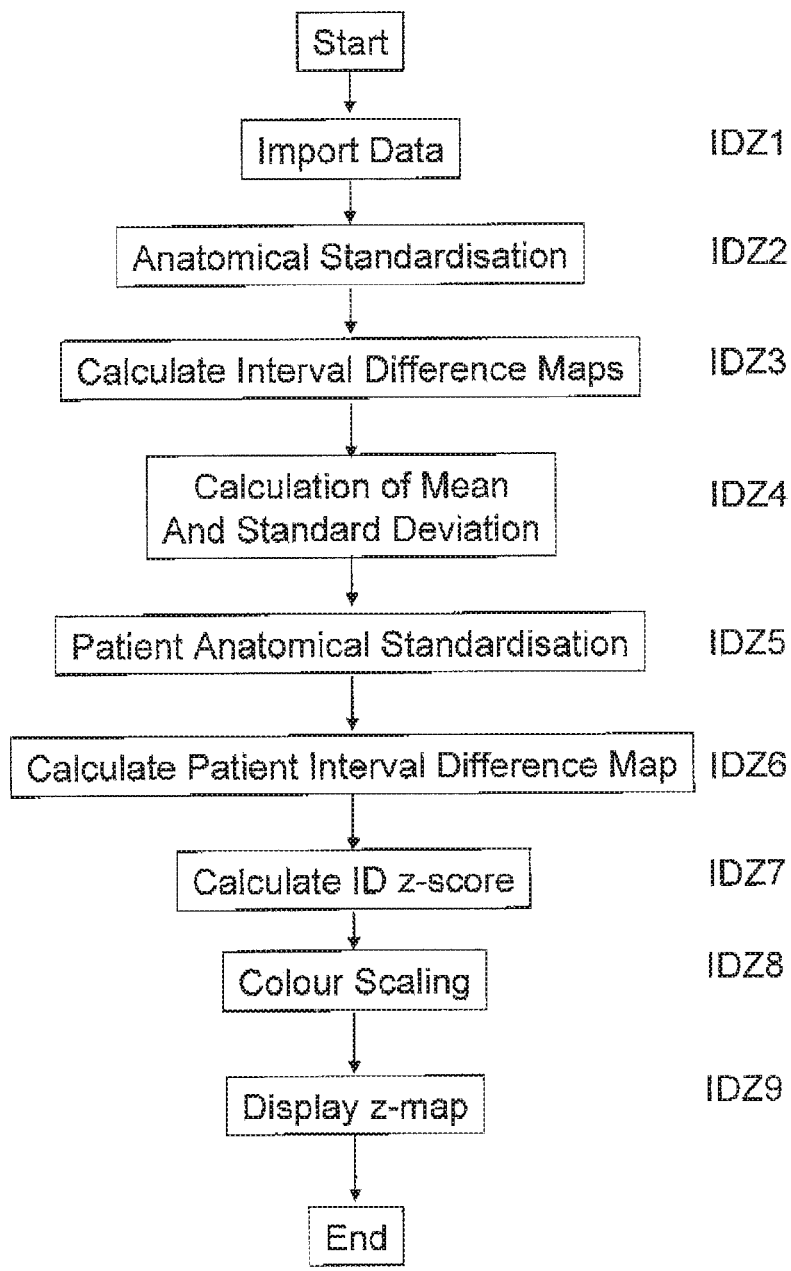

FIG. 21a is a flow chart showing a series of steps useful for producing Interval Difference (ID) z maps for a subject according to an embodiment of the invention.

FIG. 21b is table describing the nature and function of each step presented in FIG. 21a.

DETAILED DESCRIPTION OF PREFERRED EMBODIMENT

A reference atlas can be made for each the vascular response values exemplified herein, the values matched to a set of particular targeted arterial partial pressures of carbon dioxide. For example, the reference atlases can be made from $\tau$ and phase lag, for amplitude of CVR, for interval differences etc. Each can be used to generate a z map.

The terms "vasoactive response" and "vascular response" are used interchangeably.

The term "co-register" means transforming image data onto common coordinates of a standard brain using an alignment algorithm that standardizes brain size while optimizing alignment of a set of key anatomical structures.

The term "vascular reactivity" and the related term cerebrovascular reactivity (CVR) is used broadly to refer any vascular response to a standardized vasoactive stimulus, which vascular response may be a change in amplitude of the response, the time course of the response etc. Vascular response values may be a measure of the amplitude of the response (i.e. a measure of amplitude alone, wherein amplitude is revealed, for example, by allowing 3 time constants in the progress of the response to be attained before modifying the $PaCO_2^T$ or where a ramp stimulus is employed e.g. equal size increments in $PaCO_2^T$ and equal time intervals, the true amplitude of the response will be substantially revealed where, for example, two time constants in the progress of the response are attained before the next incremental change in $PaCO_2^T$.

A user may prospectively or retrospectively define a voxel as "abnormal" with reference to at least one of: (1) the size of the vasoactive stimulus or change in stimulus (e.g. the degree of upward departure of the $PaCO_2^T$ from a normal baseline value for the subject) used to reveal the abnormality; (2) the size of the z score (e.g. 2 to 3 standard deviations relative to the mean). The smaller the stimulus required to generate a deviation from the normal distribution of signals for the voxel, or the greater the signal change for a given stimulus, the more indicative of abnormality.

The time course of the response may be revealed with a step change (e.g. a targeted increase within the range of approximately 5 to 12 mm of Hg, for example 10 mm of Hg in $PetCO_2$) in the standardized vasoactive stimulus by monitoring the time course of the response to the step change.

Similarly, with respect to the amplitude of the vasoactive response at least one step change within this range or a ramp with small increments in $PaCO_2^T$ from baseline e.g. to baseline+10 mm of Hg may be used to assess the amplitude of the response.

Importantly, each $PaCO_2^T$ is maintained in the course of obtaining input of the MR signals. Accordingly the stimulus is standardized for control and test subjects and the true nature of the response is revealed. In this manner, comparing test subjects with a control subject atlas reveals the severity and distribution of an abnormal or reduced vascular response. Thus while a CVR map might show a mildly abnormal response for a voxel that is hard to judge as a probable indicator of disease, the precision of the stimulus allows a more conclusive determination of abnormality to be revealed. Herein, statistical maps such as z maps reveal the paramount importance of this standardized $PaCO_2^T$ stimulus. Furthermore a reduction in the vasoactive response, not visible in a CVR map, will be be revealed as abnormal and hence as a region that might harbour an underlying pathology.

The term "high resolution" with used with reference to imaging modality or device refers to an imaging modality enjoying a spatial resolution of 1 cubic centimeter or smaller. The term includes MRI imaging modalities (for example BOLD, T2*, ASL) and other imaging modalities well known as being useful to quantify surrogate measures of blood flow (CT, SPECT, PET). Proprietary and non-proprietary software for analyzing images in available to persons skilled in the Importantly, a standardized vasoactive stimulus is accomplished in the manner described herein.

Preferably, the standardized vasoactive stimulus is one or more targeted arterial partial pressures of carbon dioxide. Optionally, the standardized vasoactive stimulus is a series of increments or decrements in a subject's arterial partial pressure of carbon dioxide as described in our co-pending U.S. patent application Ser. No. 14/398,034 originally published as WO/2013/163735. One or more targeted increases in a subject's arterial partial pressure of carbon dioxide may also be accomplished in larger steps as described in the examples herein and more generally in our co-pending U.S. application Ser. No. 14/363,259, originally published as WO/2013/082703.

A measurable increase in the end-tidal (end-exhaled) partial pressure of $CO_2$ ($PETCO_2$) may be used as a surrogate measure for the true independent stimulus, the partial pressure of $CO_2$ in arterial blood ($PaCO_2$). Optionally, a targeted end tidal partial pressure of carbon dioxide is achieved via sequential gas delivery using a specialized re-breathing circuit or a virtual sequential gas delivery circuit (see our co-pending application No. US/2015/0034085, originally published as WO/2013/138910).

CVR may be defined as the percent change in BOLD signal (arbitrary units) per mmHg change in $PaCO_2$.

CVR values for subjects in need of assessment of cerebrovascular reactivity in at least one ROI are assigned color-coded z values based on computations of mean (+/− SD) CVR values, preferably computed on a voxel by voxel basis, for a group of control individuals using images co-registered to a standardized space based on anatomical markers and standardized parameters. The color-coded Z values representing the number of standard deviations from the mean are then superimposed, on the corresponding voxel on an anatomical scan to generate Z maps.

In one embodiment of the method, CVR was measured as the blood oxygen level dependent (BOLD), magnetic resonance imaging (MRI) response to a standardized hypercapnic stimulus. CVR maps from 46 healthy subjects were co-registered into a standard space and mean and standard deviation (SD) was measured for each voxel to form the normal CVR atlas. CVR maps from 9 patients were assigned a z-score according to the mean and SD of the corresponding voxel of the atlas. The z-scores were color coded and superimposed on their anatomical scans to form z-maps, which were assessed to determine whether they enhanced the interpretation of CVR maps.

The z-maps display of the voxel-by-voxel statistical deviation of CVR from the mean of the atlas enabled detection of reductions in CVR not apparent in CVR scans. They identified generalized, symmetrical reductions in CVR as well as quantifying the extent of abnormality in focal lesions evident on CVR maps.

The inventors have found that z-maps complement CVR maps by detecting, localizing, and assessing, the deviation from normal vascular responses.

In order to excessive repetition, it is to be understood that the various optional features described in connection with one of the various aspects and more particularized embodiments of the invention described herein, apply to other aspects/embodiments subject matter described herein including a method as defined herein, an imaging system as defined herein, an atlas as defined herein, a computer program product as defined herein, a non-transitory computer memory as defined herein etc.

The present invention extends the analytic methods of CVR measurement to determine the region by region normal range of CVR and thereby enable quantification of abnormality by the assessment of CVR in terms of its deviation from a statistical mean. The inventors took an approach similar to that of Guimond et al. [Guimond A, 2000] and Seitz et al. [Seitz, 1990] who co-registered scans of healthy subjects into a standard space and determined the normal mean and variance of CVR, voxel-by-voxel. In one aspect, the present invention is directed to generating an atlas of images for non-pathological CVR response by co-registering $CO_2$ stimulated BOLD MRI CVR maps from a healthy cohort into a standard space, and calculating the mean and SD of the CVR for each voxel.

Patient CVR maps were then also co-registered into standard space and each voxel scored positive or negative relative to the mean, and quantified by a z-score of the corresponding voxel in the atlas. These z-scores were then colour coded and superimposed on the patient's anatomical scan to generate a z-map. The inventors determined that z-maps enhance the interpretation of BOLD MRI CVR maps and highlight brain areas where vessels may have residual reactivity above the threshold for the development of steal. In particular, by comparing CVR maps and z-maps in 8 patients with symptomatic cerebrovascular steno-occlusive disease and one patient with increased intracranial hypertension it was determined that z-maps enhance the interpretation of CVR maps.

EXAMPLE 1

Studies conformed to the standards set by the latest revision of the Declaration of Helsinki and were approved by the Research Ethics Board (REB) of the University Health Network, Toronto, Ontario and all subjects gave written informed consent. Forty-six healthy volunteers were recruited for the creation of a normal CVR atlas by advertisement and word of mouth. This cohort consisted of subjects of both sexes and any age who claimed to be in good health, denied a history of neurological disease, were non-smokers, and were taking no medication. They were asked not to engage in heavy exercise or drink caffeinated drinks on the day of the scan. The characteristics of these subjects are presented in Table 1 (FIG. 12). We then drew the data from ten patients from our database of REB-approved CVR studies in patients with known symptomatic cerebrovascular disease [Spano, 2013]. Sample patients were not selected for age, sex, diagnosis, or findings on vascular imaging or CVR studies. All 10 patients were chosen and grouped before any of their data was analyzed. None were rejected after analysis.

Experimental Protocol
Hypercapnic Stimulus

The implementation of prospective end-tidal gas control has been described in detail elsewhere [Fierstra, 2013]. In brief, subjects were fitted with a face mask, and connected to a sequential gas delivery breathing circuit [Somogyi, 2005]. The patterns of $P_{ET}CO_2$ and $P_{ET}O_2$ were programmed into the automated gas blender (RespirAct™, Thornhill Research Inc., Toronto, Canada) running the prospective gas targeting algorithm of Slessarev et al. [Slessarev, 2007]. A standardized step $CO_2$ stimulus was implemented, consisting of the following sequence: a baseline $P_{ET}CO_2$ of 40 mmHg for 60 s, step to a hypercapnia of 50 mmHg for 45 s, baseline for 90 s, hypercapnia for 120 s, and return to baseline for 60 s, all during isoxic normoxia. For the healthy cohort the mean (SD) change in $P_{ET}CO_2$ was 9.2 (0.7) mmHg. This methodology wherein the subject inspires a neutral gas at the end of each breath (implemented via sequential gas delivery—see e.g. see our co-pending application No. US/2015/0034085) has been shown to control the $CO_2$ stimulus such that $P_{ET}CO_2$ is equivalent to $PaCO_2$ [Ito, 2008].

MRI Protocol and CVR Map Generation

Magnetic resonance imaging was performed with a 3.0-Tesla HDx scanner using an 8-channel phased-array receiver coil (Signa; GE Healthcare, Milwaukee, Wisconsin), and consisted of BOLD acquisitions with echo planar imaging (EPI) gradient echo (TR/TE=2000/30 ms, 3.75×3.75×5 mm voxels, field of view 24×24 cm, 39 slices, slice thickness 5 mm, matrix size 64×64, number of frames=254, flip angle (FA)=85°).

The acquired MRI and $P_{ET}CO_2$ data were analyzed using AFNI software (National Institutes of Health, Bethesda, Maryland; http://afni.nimh.nih.gov/afni; Cox, 1996 #16172]). $P_{ET}CO_2$ data was time-shifted to the point of maximum correlation with the whole brain average BOLD signal. A linear, least-squares fit of the BOLD signal data series to the $P_{ET}CO_2$ data series (i.e., CVR) was then performed on a voxel-by-voxel basis. For displaying CVR maps, voxels with a correlation coefficient between −0.25 and +0.25 were eliminated before color-coding the remaining CVR values (see spectrum in FIG. 3).

BOLD images were then volume registered and slice-time corrected and co-registered to an axial 3-D T1-weighted Inversion-Recovery prepared Fast Spoiled Gradient-Echo (IR-FSPGR) volume (TI/TR/TE=450/8/3 ms, voxel size 0.86×0.86×1.0 mm, matrix size 256×256, field of view 22×22 cm, slice thickness=1 mm, FA=15°) that was acquired at the same time [Saad, 2009]. This method has been described in greater detail elsewhere [Fierstra, 2010].
Analysis of CVR Maps
Constructing the Atlas (see also Guimond, A 2000, and Seitz, 1990).

Analytical processing software (SPMS; Wellcome Department of Imaging Neuroscience, University College, London, UK; http://www.fil.ion.ucl.ac.uk/spm/software/spm5), was used to co-register each of the individual brain volumes from the healthy cohort into MNI (Montreal Neurologic Institute) standard space using a 12-parameter [Ashburner,1997] affine transformation followed by nonlinear deformations to warp the brain volume of interest into an MNI template of identical weighting contrast. The T1-weighted FSPGR volume was used to estimate the transformation normalization into standard space, as defined by a T1-weighted MNI152 standard template [Ashburner, 1999].

A spatial smoothing of Full-Width Half-Maximum (FWHM) 5 mm was applied to each voxel. Assumption for normality was tested using the Anderson-Darling test (the statistical test for normality provided in AFNI) with p values greater than 0.05 assumed to pass the test. As most voxels (60%) did pass this threshold, and these were diffusely distributed throughout the brain, the simplifying assumption was made that the CVR for each voxel was normally distributed. The mean ($\mu$) and associated standard deviation ($\sigma$) of CVR was calculated (AFNI software [Cox, 1996]). Maps were then constructed for $\mu$ and coefficient of variation ($\sigma/\mu$) to characterize the atlas.
CVR Z-Map Generation The generation of an individual's CVR z-map consisted of three steps. First, a spatial normalization of the individual's anatomical scan and CVR map [Ashburner,1999] using a MNI152 SPM distributed template was produced. Second, the CVR of each voxel (x) was scored in terms of a z value (i.e., $z=(x-\mu)/\sigma$). Finally, a color was assigned to each z score (see scale in FIG. 3) to indicate the direction and magnitude (in z values) of the differences from the mean of the corresponding atlas voxel. CVR and CVR z scores were superimposed on the corresponding anatomical scans to allow comparison of the CVR and its z score. Note that CVR voxels that are positive but lower than the atlas mean for that voxel will have negative z scores. Greater specificity for identifying underlying vascular pathophysiology was assumed to be connoted by greater absolute value of z scores and the confluence of similarly scored voxels in both CVR and CVR z-maps.

To clarify the colour coding used, it is pointed out that in the resulting z-map: (1) Patient CVR map voxels that are negative (blue) where the corresponding atlas CVR map voxels are positive, will have negative z-scores coded light blue to purple. (2) Patient CVR voxels that are positive but lower than the atlas CVR voxels will also have negative z-scores. (3) However, negative CVR voxels that are greater (towards the positive direction) than the corresponding atlas CVR voxel will nevertheless have a positive z-score. Greater specificity is connoted by greater z scores (for z-maps) and the confluence of similarly scored voxels (both CVR and z-maps).
Z-Map Normal Cohort CVR Characteristics FIG. 1 shows maps of the mean CVR and coefficient of variation (CV) of the reference atlas. Voxels over predominantly cortical gray matter (GM) have mean CVR of 0.20 to 0.30% $\Delta$BOLD/$\Delta$ mmHg whereas those over predominantly white matter (WM) had considerably lower CVR (0.05 to 0.15% $\Delta$BOLD/$\Delta$ mmHg). Many voxels had mixed tissue type content, so that intermediate CVR values at the interface probably represents voxels that had greater overlap between WM and GM. Clusters of highest mean CVR values were found over veins.

With respect to variability, GM areas had the lowest CV values, ranging between 30-40%, whereas higher CV values, between 50-60%, were found in WM. The high CV values calculated at the outer margin of the brain result from the variation in CVR measured where that voxel is predominantly GM, CSF, bone, WM, and blood vessels in different subjects. Similarly, venous sinuses were difficult to localize consistently.

Figure 2:
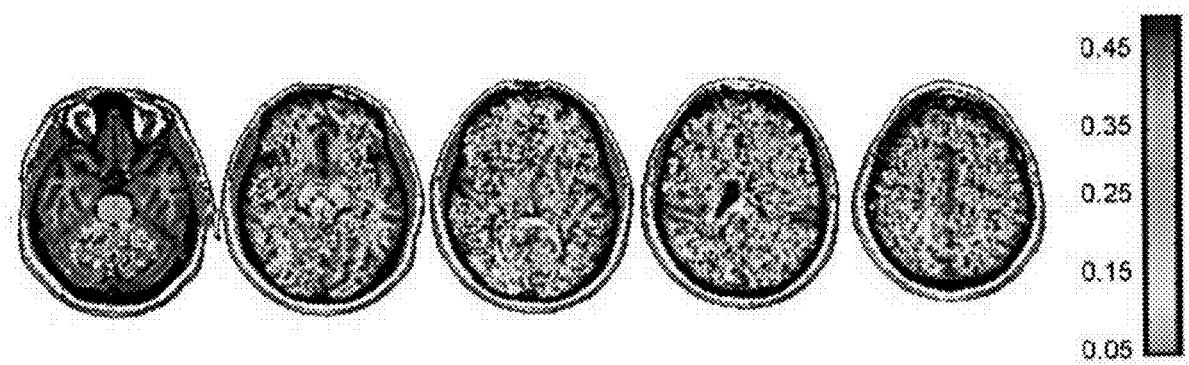
FIG. 2 is a set of axial slices displaying the spatial p-value results of an Anderson-Darling normality test. The spatial distribution of the results this test was applied to the CVRs of the 46 healthy subjects CVRs graphed onto the MNI standard brain. At least 60% of the voxels had a p-value greater the 0.05; these voxels were fairly evenly distributed throughout the brain.

The spatial distribution of the results of the Anderson-Darling statistical test of normality applied to the 46 healthy subjects CVRs graphed into the MNI standard brain is shown in FIG. 2. At least 60% of the voxels had a p-value greater the 0.05; these voxels were fairly evenly distributed throughout the brain.

Figure 3:
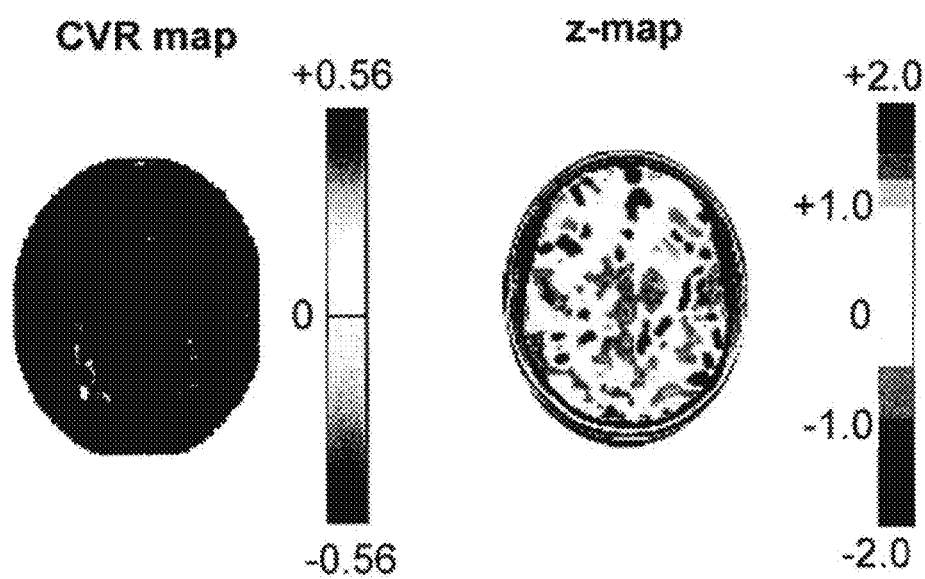
FIG. 3 is a healthy subject's CVR map. An axial slice is shown on the left displaying the spatial distribution of CVR values coloured according to the scale shown on the right in % BOLD change/mmHg $P_{ET}CO_2$ change. The corresponding CVR z-map and its color scale are shown on the right. The CVR z-map provides a perspective on the (statistical) normality of CVR in the CVR map.
Figure 4:
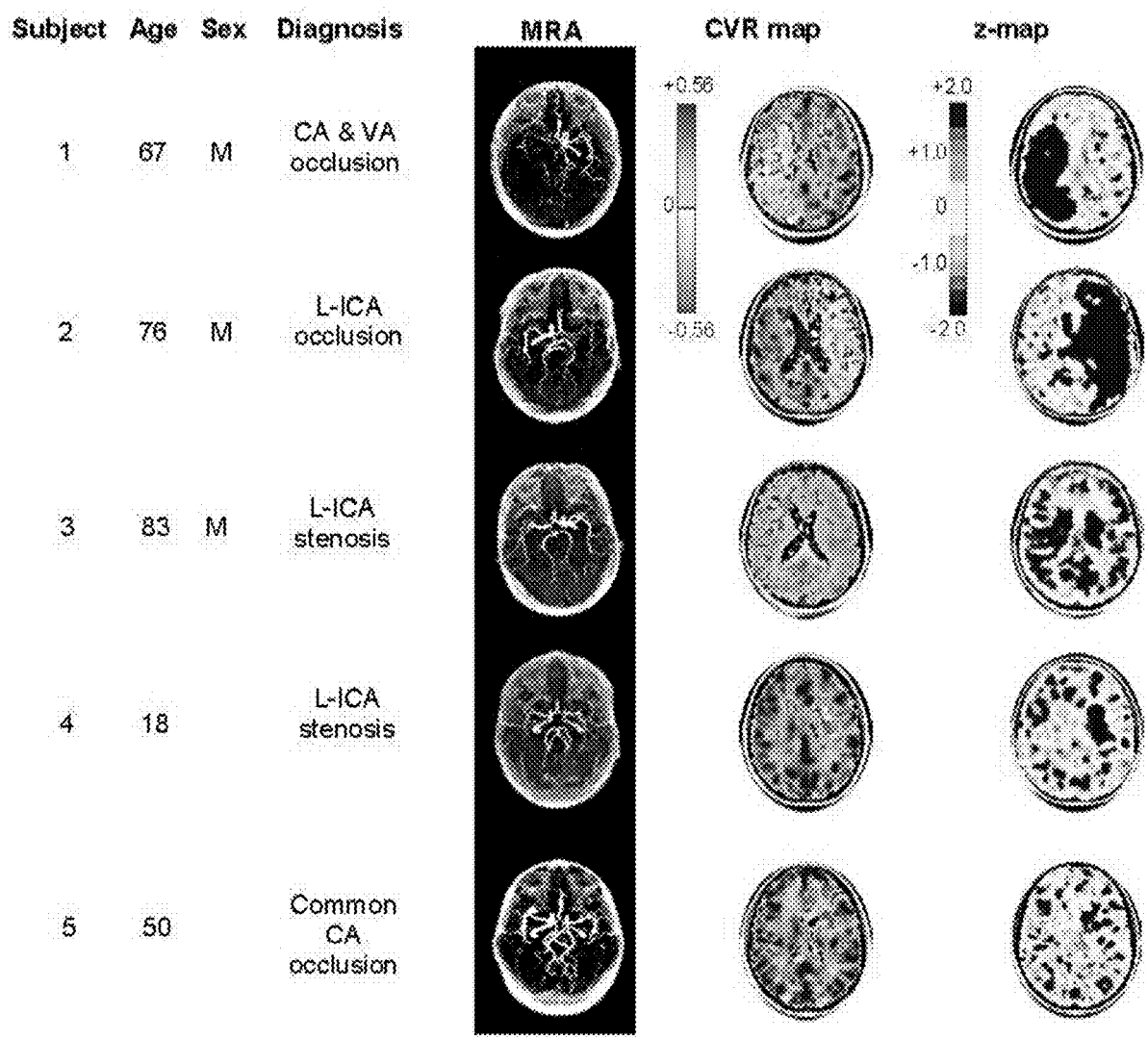
FIG. 4 depicts magnetic resonance angiograms, CVR maps and corresponding z maps for a sample set of 5 patients with varying levels of carotid artery (CA) disease. The CVR maps were analyzed by z scoring of the CVR map relative to a normal atlas. This figure is supplemented with a table, Table 2 (FIGS. 6A and 6B) that provide additional information and commentary for each subject. (Dx.=diagnosis; MRA=magnetic resonance angiogram).
Figure 5:
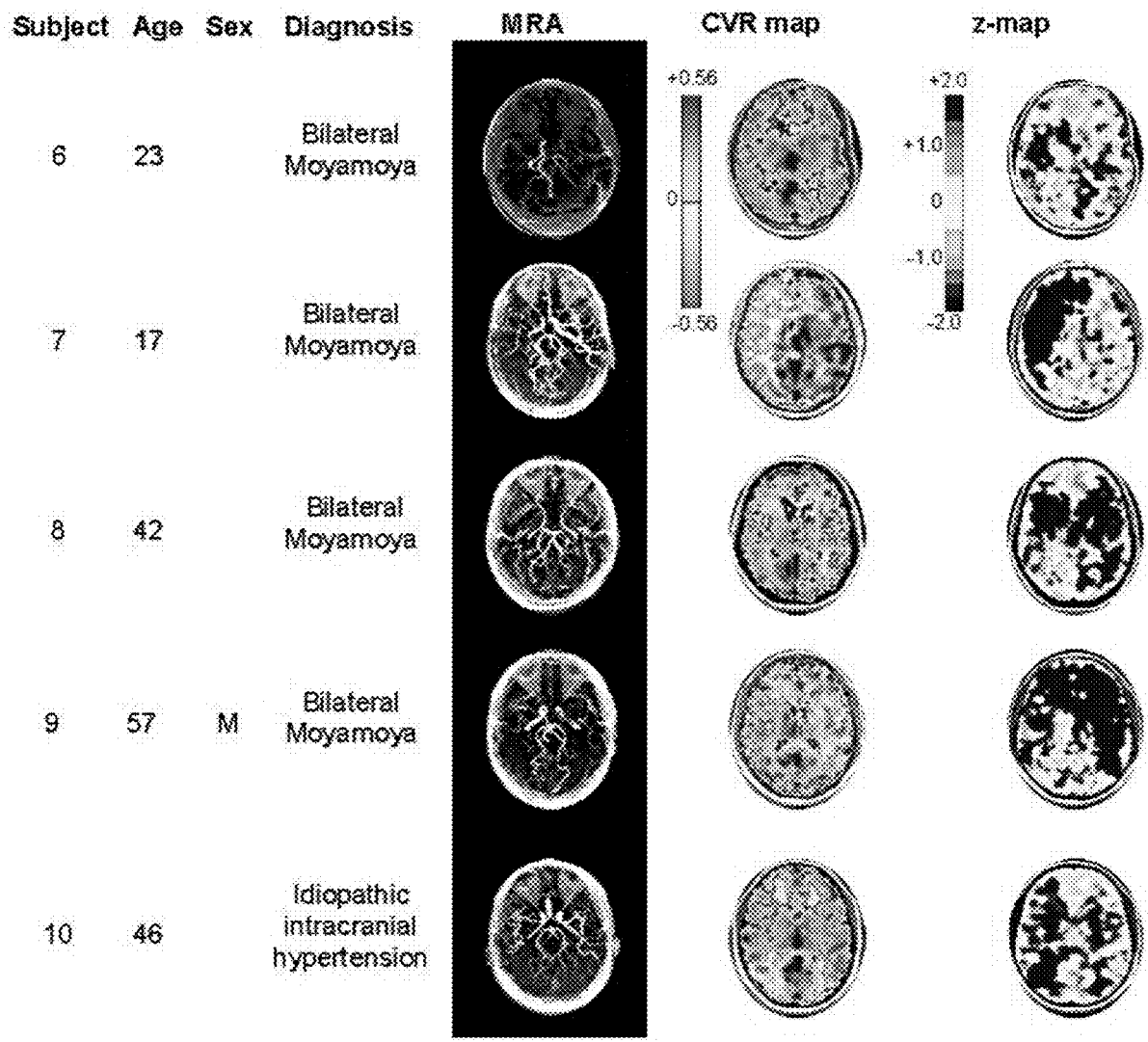
FIG. 5 depicts magnetic resonance angiograms, CVR maps and corresponding z maps for a sample set of 4 patients with Moyamoya disease and one patient with idiopathic intracranial hypertension. The CVR maps were analyzed by z scoring the CVR map relative to a normal atlas.

For comparison purposes, FIG. 3 presents the CVR and its accompanying z-map from a healthy subject not included in the atlas. The z-maps of the 10 patients drawn from our database are shown in FIGS. 4 and 5, and descriptions related to each patient are presented in Table 2 (FIGS. 6A and 6B).

Z-scoring the CVR studies in our sample patient cohort provided an objective, graded demarcation of the reduction in CVR, quantified relative to the normal range for the region. The z-map therefore emphasized the CVR changes attributable to underlying vascular pathophysiology. This approach diverges significantly from previous practice where CVR was divided into 'steal and non-steal' territories [Fierstra, 2010] [Balucani, 2012] or compared to normal atlases where thresholded CVR values of 2 [Commowick, 2008] and 3 [Kemp, 1995] standard deviations were required to identify significant differences from normal.

Our method identifies a graded range of reductions in CVR that do not meet all of the conditions required for steal, yet nevertheless represent vascular pathophysiology [Sobczyk 2014]. Furthermore, we minimized the inter-subject variability (i.e., 'noise') due to diversity of technical specifications and brain physiology by standardizing both MRI sequences and the provocative stimulus across the atlas and patient studies. A secondary outcome of the study is that the calculation of the voxelwise mean and variance, characterizes the magnitude and variance of normal CVR in humans, as represented by our sample cohort.

Previous studies examined the deviation from steady state, and therefore reflected only the combined subject-to-subject, and the test-to-test variability [Seitz, 1990]. In contrast, CVR requires the application of a stimulus and the measurement of a response to that stimulus, both potentially adding variations to the CVR values in the atlas. Of these, we can only address the issue of variability in the stimulus, leaving the variation of response to be reflected as a characteristic of the atlas.

First, we wished to retain the advantage of the high spatial and temporal resolution provided by BOLD signal [van der Zande, 2005] as the surrogate for CBF; for this, the application of the stimulus had to be MRI compatible. Second, whereas the magnitude of the stimulus—i.e., the change in $PaCO_2$—is unknown with other hypercapnic methods (Fierstra, 2013), it is precisely known with our method of stimulus generation [Ito, 2008 #14395]. This methodology therefore enables the reduction of the effects of variations in the stimulus on CBF by (a) normalizing the change in BOLD signal for the change in $PaCO_2$ and (b) implementing a uniform change in $PaCO_2$ [Fierstra, 2013] between patients and atlas.

Characteristics of the Patient Cohort

The examination of our patient data illustrated the value added to CVR interpretation by z-maps surprisingly underscoring the importance of a standardized vasoactive stimulus. Subjects 3, 6, 8, and 10, in FIGS. 4 and 5 illustrate the difficulty in confidently interpreting abnormal CVR in areas not showing steal. In patients 3 and 6, the reductions in CVR are symmetrical; there is little 'steal' as no territory is strong enough to be the 'thief' [Sobczyk, 2014]. This mechanism can also explain the small negative CVR values despite profound reductions in CVR z scores in subjects 8 and 10. In subjects 4, and 5, the robust CVR is likely due to the recruitment of collateral blood flow, and had been interpreted as 'normal' in the original studies. However, the z-map analysis now highlights a previously unappreciated reduction in CVR in the left MCA territory. A summary of the clinically relevant advantages z-maps provide beyond plain CVR maps is presented in Table 3 (FIG. 7)

We also note that most of the patients presented with protean transient symptoms and were otherwise remarkably asymptomatic. We are impressed that the extent of the neurovascular changes that were provoked by the hypercapnic challenge are very much out of proportion to the clinical symptoms, indicating the considerably greater sensitivity of neuroimaging, including CVR, in detecting occult neurovascular disease compared to clinical assessment.

Characteristics of the Reference Atlas

The CVR atlas represents the distribution of CVR and its variance in the human brain, as reflected in our sample. It incorporates and reflects the regional anatomical differences in the response of the BOLD signal resulting from (a) tissue factors, such as age, sex, $O_2$ consumption, capillary density, changes in blood volume, differences in blood arrival time, and vascular response time; (b) physiologic factors such as genetic makeup, variations in diet, sleep pattern, time of day, hormonal level, physical fitness, blood pressure and blood pressure response to hypercapnia, state of mind; and (c) unknown technical and mechanical changes in the MRI system over time. These form the background "noise", from which a patient's abnormal voxels, their distribution and the extent of their deviation, must be discerned.

To optimize sensitivity, the subject-to-subject variability in the atlas can be minimized by targeting the atlas to a particular patient group. For example, matching age, sex, medication, and other physiologic features to the target study group (for example young men with multiple sclerosis), and reducing all technical and methodological sources of variability—would leave the disease process as the dominant source of divergence of CVR from that of the reference cohort.

Z-Maps to Compare CVR Across Platforms

An important feature that favours the normal atlas and z-map approach is that its value does not depend on the MRI sequence used or the actual method of administering the vasodilatory stimulus—dose of acetazolamide, inspired concentration of $CO_2$, or breath hold time—rather it is the consistency of the acquisition sequence and the stimulus within the atlas population and between the atlas and the target subjects that is revealed to be important (see [Fierstra, 2013]). Under these conditions, z values should be comparable across platforms.

Pooling atlases from multiple scanners may also address this issue but would also increase the atlas variability and therefore reduce its sensitivity. We therefore suggest that at least initially, it is safest to generate a unique atlas for each scanner. On the positive side, doing so can be seen as a one time 'calibration'. Since it accounts for between-subject variability the, z-map approach provides a robust control group that can be referenced for several studies, and thereby maximize the statistical power of the subject cohort, and minimizing the number of subjects required.

We accepted the large age range in our atlas. Nevertheless, it was characteristic of the age range of our patient database. Any discrepancies in matching would optimize the specificity. Sensitivity in picking up pathology in our patient cohort was not a concern as our experiences lead us to expect that the changes in CVR due to cerebrovascular disease will greatly exceed that between healthy subjects in an atlas, regardless of the sex and age distribution [Oudegeest-Sander, 2013]. We did however minimize the variability by using a single scanner, running the same MRI acquisition sequence for all subjects and patients, and implementing a uniform stimulus.

These example patients we chose were not intended to represent typical findings for any particular pathology, but to illustrate the range of images produced by z-score analysis relative to a reference atlas. We anticipate that different neurological diseases may call for different stimulus patterns, and so specific normal atlases to reveal their pathophysiology. It will be appreciated that certain patterns (square wave, sinusoidal, ramp, pulse, and others) may be optimum to study certain conditions (vasculitis, traumatic brain injury, subarachnoid hemorrhage and others). The overarching approach nevertheless would be the same: compare patient CVR maps to that of a reference atlas.

Construction of the Interval Difference (ID) Atlas

Twelve males with a mean (SD) age of 35(14.3), were selected from the healthy cohort to repeat their CVR measurement within a two week timeframe, within which it is assumed that no disease process was initiated and all physiologic differences are those that occur in healthy people day to day. Construction of the ID-atlas proceeded as described for the normal atlas except that in this case we first calculated a voxel-by-voxel difference in CVR between the repeated studies in each of the 12 subjects.

MRI Protocol and CVR Map Generation

Magnetic resonance imaging was performed with a 3.0-Tesla scanner (Signa; GE Healthcare, Milwaukee, Wisconsin) and consisted of BOLD acquisitions with echo planar imaging (EPI) gradient echo (TR 2000, TE 30 ms, 3.75× 3.75×5 mm voxels).

The acquired MRI and $P_{ET}CO_2$ data were analyzed using AFNI software (Cox, 1996). $P_{ET}CO_2$ data were time-shifted to the point of maximum correlation with the whole brain average BOLD signal. A linear, least-squares fit of the BOLD signal data series to the $P_{ET}CO_2$ data series was then performed on a voxel-by-voxel basis. The slope of the relation between the BOLD signal and the $P_{ET}CO_2$ was color-coded to a spectrum of colors corresponding to the direction (positive or negative) and the magnitude of the correlation to create CVR maps. Voxels with correlation coefficients between −0.25 to +0.25 were thresholded out of the maps. BOLD images were then volume registered and slice-time corrected and co-registered to an axial 3-D T1-weighted Inversion-Recovery prepared Fast Spoiled Gradient-Echo (IR-FSPGR) volume (voxel size 0.86×0.86× 1.0 mm) that was acquired at the same time (Saad et al., 2009). This method has been described in greater detail by Fierstra et al. (Fierstra et al., 2010).

Analytical processing software (SPMS; Wellcome Department of Imaging Neuroscience, University College, London, UK; http://www.fil.ion.ucl.ac.uk/spm/software/spm5), was used to co-register each of the healthy individual cohort brain volumes into MNI (Montreal Neurologic Institute) standard space using a 12-parameter (Ashburner and Friston, 1997) affine transformation followed by nonlinear deformations to warp the brain volume of interest into an MNI template of identical weighting contrast. The T1-weighted FSPGR volume was used to estimate the transformation normalization into standard space, as defined by a T1-weighted MNI152 standard template (Ashburner and Friston, 1999). A spatial smoothing of FWHM 5 mm was applied to each. Finally, the mean CVR ($\bar{r}$) and associated standard deviation ($\sigma_r$) was calculated for each voxel (AFNI software (Cox, 1996)).

Repeatability and Construction of the Interval Test Difference (ID) Atlas

Twelve males with a mean (SD) age of 35(14.3), were selected from the healthy cohort to repeat their CVR measurement within a two week timeframe. To obtain regional measures of CVR, we segmented the anatomical images into gray matter and white matter (SPMS; Wellcome Department of Imaging Neuroscience, Institute of Neurology, University College, London, UK) regions and spatially normalized to CVR maps. Time comparisons were evaluated by Bland-Altman plots and the coefficient of variation (CV) for grey and white matter as estimates of repeatability (SigmaPlot 12.5, Systat Software, California).

Construction of the ID-atlas proceed as described for the normal atlas except that in this case we first calculated a difference CVR map from the two time points in each of the 12 subjects. Then from the difference maps, we calculated a difference mean, and associated standard deviation for each voxel to produce the test-retest difference probability atlas (ID-atlas).

Z-Maps

To compare an individual CVR map with that of the normal or temporal atlas the spatial CVR information was further analyzed by comparing the direction and magnitude of the change in BOLD signal of each voxel to that of the corresponding voxel in the atlas; the resulting map was called a z-map. This comparison consisted of three steps. First, a spatial normalization of the patient anatomical and CVR scan (Ashburner and Friston, 1999) using a MNI152 SPM distributed template supplied by the Montreal Neurological Institute was produced. Second, the CVR of each voxel was scored in terms of a z value (i.e., the value expressed in standard deviations (SD) of the CVR scores of the corresponding voxel in the atlas, $$\left(z = \frac{r - \bar{r}}{\sigma_r}\right).$$

Finally, a color was assigned to each z-score; AFNI software (Cox, 1996) to indicate a magnitude and direction of the differences in z-scores compared to the atlas population. Positive scores (where the CVR is greater than the mean of the atlas) were coloured green with 15 different shades ranging in intensity between 0 to 3.0 SD. Negative scores (where CVR is less than the mean) were coloured purple with 15 shades ranging in intensity between 0 and −3 SD.

The calculated z-scores were superimposed on the anatomical scans to allow comparison of the patient's CVR to the atlas CVR. As a result: (1) Patient CVR map voxels that are negative (blue) where the corresponding atlas CVR map voxels are positive, will have negative z-scores. (2) Patient CVR voxels that are positive but lower than the atlas CVR voxels will also have negative z-scores. (3) Negative CVR voxels that are higher than the corresponding atlas CVR voxel will have a positive z-score. Maps with z-score thresholds <0.5 SD provide highest sensitivity and those >2.0 SD greatest specificity.

CVR differences over time were calculated for two patients who underwent more than one CVR study in a year time span (ID z-maps). Z-scores were calculated voxel-by-voxel by comparing the difference CVR map of the patient to the temporal atlas. This allowed us to evaluated changes over time that differed significantly from changes over time found in a normal cohort.

We examined the ID z maps generated from our small trial atlas in the most recent 15 patients in our database that met the search criteria. We studies two illustrative cases in detail (one patient who had undergone several scans before undergoing extracranial-intracranial (EC-IC) bypass, and one patient with symptomatic Moyamoya disease that had undergone several CVR studies over a 2 year period).

Figure 8:
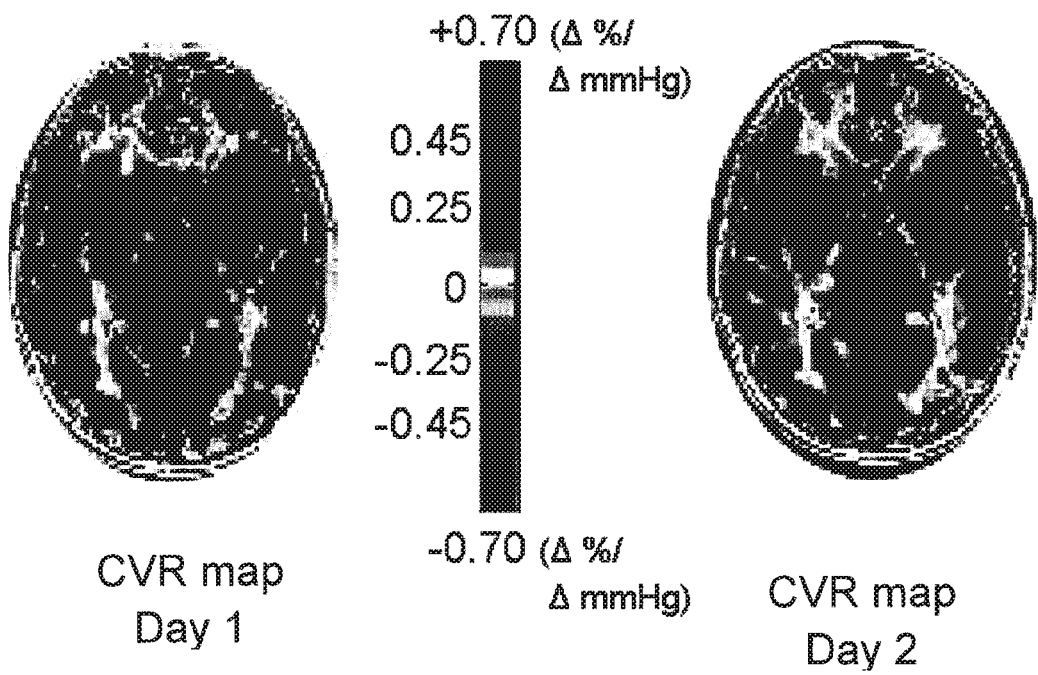
FIG. 8 shows CVR maps for a male subject tested on two different sessions 14 days apart.

On average the healthy subjects who participated in the testing for the temporal atlas were scanned 15 days apart. FIG. 8 illustrates the reproducibility of the CVR map vascular response pattern for one example subject.

Figure 9:
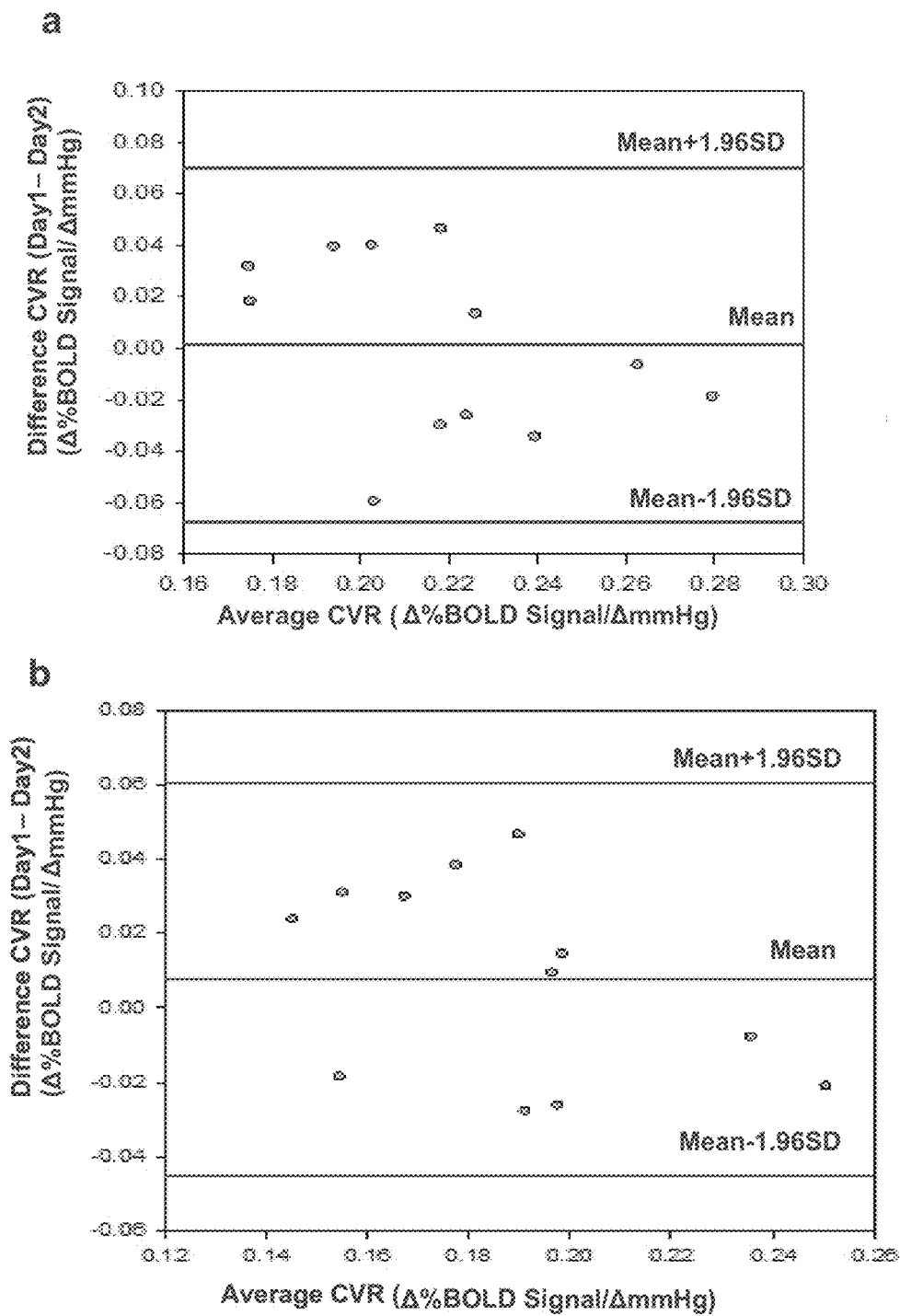
FIG. 9 are Bland-Altmann plots of CVR for between-day reproducibility for gray (a) and white (b) matter regions. The Bland-Altman analysis compares the CVR values for gray and white matter obtained on the different days establishing that the mean difference between days for gray matter was 0.0013 (Δ % BOLDSignal/ΔmmHg), with limits of agreement of −0.0674 and 0.0700 (±1.96 SD); whereas the mean difference between days for white matter was 0.0078 (Δ % BOLDSignal/ΔmmHg) with −0.0449 and 0.0605 (±1.96 SD) limits of agreement.

FIG. 9 presents the results of a Bland-Altman analysis comparing the CVR values for gray and white matter obtained on the different days. The mean difference between days for gray matter was 0.0013 (Δ % BOLDSignal/ΔmmHg), with limits of agreement of −0.0674 and 0.0700 (±1.96 SD). The mean difference between days for white matter was 0.0078 (Δ % BOLDSignal/ΔmmHg) with −0.0449 and 0.0605 (±1.96 SD) limits of agreement.

The mean CVR and CV reproducibility measures for gray and white matter are presented in the Table immediately below. The reproducibility analysis demonstrates good reproducibility between-day CVR estimates in both gray (CV=10.25%) and white matter (CV=9.66%) on average.

TABLE

Mean (SD) CVR differences between days and mean (SD) coefficient of variation (CV) for the gray and white matter regions.

|  | Gray Matter | White Matter |
| --- | --- | --- |
| Mean CVR difference (Δ % BOLD/ΔmmHg) | 0.2179 (0.021) | 0.1882 (0.017) |
| Mean CV (%) | 10.25 (5.19) | 9.66 (4.81) |

ID Z-Map

Figure 10:
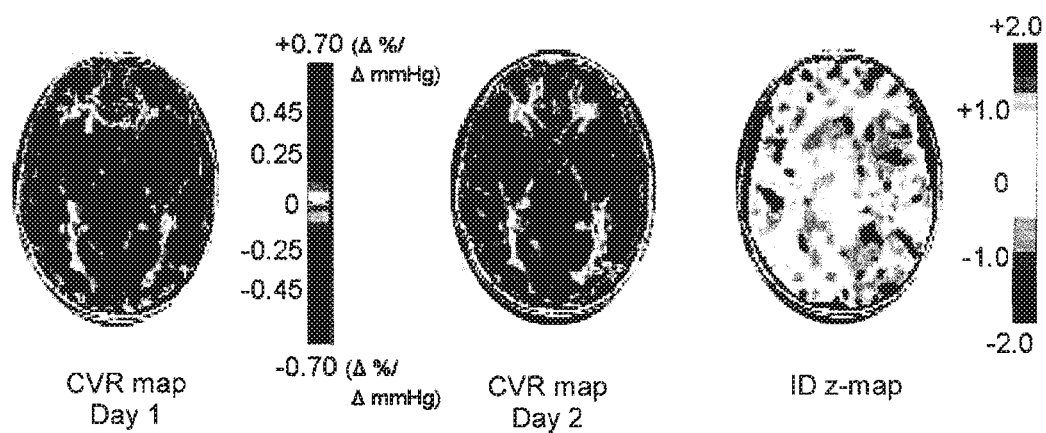
FIG. 10 depicts results for the application of a sample ID atlas to assess the changes in CVR over time in a healthy control subject (not included in the ID atlas) demonstrating that the majority of difference between day 1 and day 2 in this healthy subject <1.0 SD as expected.

FIG. 10 represents the application of our sample ID atlas to assess the changes in CVR over time in a normal subject not included in the ID atlas. We can see that the majority of difference between day 1 and day 2 in the healthy subject <1.0 SD as expected.

Figure 11:
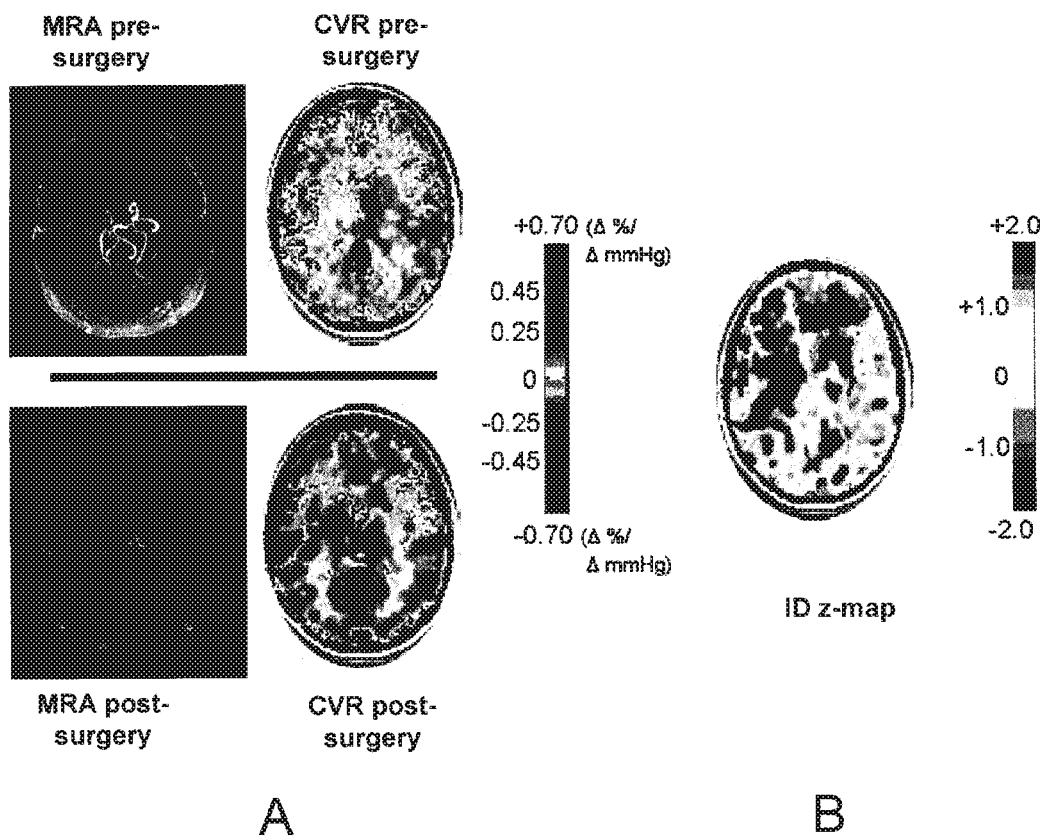
FIG. 11 presents angiogram, CVR and ID z maps for an axial slice showing the spatial distribution of CVR values and the associated z-maps at z value thresholds of 0.5 and 1.0. Imaging data from a 38 year old female with moya moya cerebrovascular disease who underwent 2 CVR studies pre, and 6 months post right EC-IC bypass, 6 months apart. A) The magnetic resonance angiogram and CVR maps for an axial slice showing the spatial distribution of CVR values B. The temporal z-maps of the two CVR maps.

FIG. 11 represents an example of the application in a patient from our database. The patient was a 38 year old female who was diagnosed with bilateral moya moya and had a right EC-IC bypass. A CVR was preformed both pre- and post-surgery. CVR pre-surgery (FIG. 11A) displays severe right side impairment with decreased CVR in the left MCA territory. Post-surgery CVR suggests that the bypass on the right side reversed the steal and improved the flow, resulting in steal from the left MCA territory.

The z-maps provide additional information, suggesting that the areas of impaired CVR on the left have in fact improved after surgery when compared to a normal cohort. The ID atlas was then applied to determine whether the z-map changes could be due to variability in the testing over time rather than the intervention (FIG. 11B). The ID z-maps confirmed, and gave an indication of the extent and distribution of, changes in CVR.

Identifying pathophysiology and distinguishing changes over time is capable of determining the voxelwise probability of a true, clinical interval change in CVR between two scans. The above described z-maps consisted of a database of voxelwise mean and standard deviation of CVR suitable for identifying the probabilities and extent of abnormality of CVR. Z-maps can be thresholded to alter the balance of sensitivity and specificity in identifying abnormal voxels. Identifying significant changes in a single subject as the voxel statistic does not depend on when the scan is performed, and thus includes the test to test variability. Therefore according to one aspect of the invention, we separately determined, voxel-by-voxel, location-specific statistical probabilities for changes between scans not attributable to technological and physiological variability. This capability of identifying changes between scans is useful for carrying out longitudinal studies such as following the progress of disease and the effects of interventions. As with z-maps, the range of thresholds from 0.5 to 2.0 would provide a range of high sensitivity, low specificity to high specificity, low sensitivity. We used a sample atlas of scan-to-scan differences in 12 healthy male subjects which we used to evaluate 15 patients in our database with known cerebrovascular disease. Greater sensitivity would accrue the more the subjects used in the atlas reflect factors that affect CVR in the target population; greater specificity would accrue from larger cohort numbers and wider inclusion criteria in the atlas population.

Technical and Physiological Sources of Variability in Z Maps

The concept of a voxel-by-voxel comparison of the intensity of an image to that of a normal cohort has been extensively explored (Commowick et al., 2008; Kemp et al., 1995; Laliberte et al., 2004), but it has not been applied to CVR using BOLD MRI as a surrogate for cerebral blood flow.

Minimizing Variability in CVR Due to Variation in the Stimulus

The infusion of pharmacologic agents result in a variability of blood levels, even to a standard dose; there is also a variation of vasodilatory response to a given blood level of drug (see (Fierstra et al., 2013) for discussion). Hypercapnia may result in a more reliable response to a blood partial pressure of $CO_2$ (Pa$CO_2$), the stimulus affecting cerebral blood flow (Kety and Schmidt, 1948); but attaining a repeatable Pa$CO_2$ is difficult. Infusing $CO_2$ into a face mask, (Markus and Harrison, 1992) inhaling a fixed concentration of $CO_2$, (van der Zande et al., 2005) or simply breath holding (Silvestrini et al., 1999) are not reproducible, and cannot even provide a reliable measure of the change in the Pa$CO_2$ (Hoskins, 1990; Mark et al., 2010; Prisman et al., 2007; Sasse et al., 1996). In this study we used a computer-controlled gas blender to prospectively target P$_{ET}CO_2$, which has equilibrated with the Pa$CO_2$ (Ito et al., 2008). This allowed us to repeatedly administer a standardized stimulus (from baseline P$_{ET}CO_2$ was 40.2±1.1 (SD) mmHg to 49.9±1.5 mmHg), minimizing the variability in the atlas and in the patient scans attributable to variability of the stimulus and optimizing the sensitivity of detecting interval changes in CVR.

Accounting for the Variability in CVR Due to Variation in the Signal

Despite the precise designation of the MRI scanning sequences and data analysis, there are technical causes for variation in the CVR. During signal acquisition, the signal is affected in random ways due to drift; there may be a drift in signal over time affecting all voxels and separate drift in individual voxels. This drift is usually described by a polynomial and has no consistent pattern or direction with time over the long term. Thus ID z maps provide a confidence interval for identifying changes outside those attributable to technical and physiologic (day-to-day physiology or vasodilatory stimulus) signal changes. As the technical issues result in highly variable changes voxel by voxel, one would expect the observation of systematic changes in contiguous voxels—even if small compared to day-to-day variability—to reflect pathophysiologic changes. Thus, like with the z maps, different balance between sensitivity and specificity may occur at different thresholds.

Change in CVR over time in two patients with cerebrovascular disease We presented the clinical course of two patients with steno-occlusive disease in intracranial vessels. In both cases, the symptoms were mild and transient. In contrast, the stenosis of the intracranial vessels as seen by angiography, were relentlessly progressive. The CVR values were more nuanced, reflecting the balance of blood flow resulting from the establishment of spontaneously developing, and surgically established, collateral blood flow. The total blood flow in both patients apparently remained above the threshold required to sustain neuronal function and cellular integrity preventing an acute stroke as gauged by the absence of ischemia and absence symptoms during follow-up examination. In these patients, the advanced analysis of the CVR data the ID z maps introduced in this paper ostensibly improved the resolution of underlying subclinical pathophysiologic changes not apparent from angiography and CVR maps alone.

References identified herein are hereby incorporated by reference.

REFERENCE LIST

Commowick O, Fillard P, Clatz O, & Warfield S K (2008). Detection of DTI white matter abnormalities in multiple sclerosis patients. *Med Image Comput Comput Assist Interv* 11, 975-982.

Cox R W (1996). AFNI: software for analysis and visualization of functional magnetic resonance neuroimages. *Comput Biomed Res* 29, 162-173.

Harper A M & Glass H I (1965). Effect of alterations in the arterial carbon dioxide tension on the blood flow through the cerebral cortex at normal and low arterial blood pressures. *J Neurol Neurosurg Psychiatry* 28, 449-452.

Hoskin P J, Abdelath O, Phillips H, Gilligan S, Saunders M I, Broderick P, & Baddeley H (1999). Inspired and expired gas concentrations in man during carbogen breathing. *Radiother Oncol* 51, 175-177.

Ito S, Mardimae A, Han J, Duffin J, Wells G, Fedorko L, Minkovich L, Katznelson R, Meineri M, Arenovich T, Kessler C, & Fisher J A (2008). Non-invasive prospective targeting of arterial P(CO2) in subjects at rest. *J Physiol* 586, 3675-3682.

Kassner A, Winter J D, Poublanc J, Mikulis D J, & Crawley A P (2010). Blood-oxygen level dependent MRI measures of cerebrovascular reactivity using a controlled respiratory challenge: reproducibility and gender differences. *J Magn Reson Imaging* 31, 298-304.

Kazumata K, Tanaka N, Ishikawa T, Kuroda S, Houkin K, & Mitsumori K (1996). Dissociation of vasoreactivity to acetazolamide and hypercapnia. Comparative study in patients with chronic occlusive major cerebral artery disease. *Stroke* 27, 2052-2058.

Kemp P M, Houston A S, Macleod M A, & Pethybridge R J (1995). Cerebral perfusion and psychometric testing in military amateur boxers and controls. *J Neurol Neurosurg Psychiatry* 59, 368-374.

Kety S S & Schmidt C F (1948). The effects of altered arterial tensions of carbon dioxide and oxygen on cerebral blood flow and cerebral oxygen consumption of normal young men. *J Clin Invest* 27, 484-492.

Kleiser B, Krapf H, & Widder B (1991). Carbon dioxide reactivity and patterns of cerebral infarction in patients with carotid artery occlusion. *J Neurol* 238, 392-394.

Kuroda S, Houkin K, Kamiyama H, Mitsumori K, Iwasaki Y, & Abe H (2001). Long-term prognosis of medically treated patients with internal carotid or middle cerebral artery occlusion: can acetazolamide test predict it? *Stroke* 32, 2110-2116.

Laliberte J F, Meunier J, Mignotte M, & Soucy J P (2004). Detection of diffuse abnormal perfusion in SPECT using a normal brain atlas. *Neuroimage* 23, 561-568.

Lundar T, Lindegaard K F, Froysaker T, Aaslid R, Grip A, & Nornes H (1985). Dissociation between cerebral autoregulation and carbon dioxide reactivity during nonpulsatile cardiopulmonary bypass. *Ann Thorac Surg* 40, 582-587.

Mandell D M, Han J S, Poublanc J, Crawley A P, Fierstra J, Tymianski M, Fisher J A, & Mikulis D J (2011). Quantitative Measurement of Cerebrovascular Reactivity by Blood Oxygen Level-Dependent MR Imaging in Patients with Intracranial Stenosis: Preoperative Cerebrovascular Reactivity Predicts the Effect of Extracranial-Intracranial Bypass Surgery. *AJNR Am J Neuroradiol* 32, 721-727.

Mandell D M, Han J S, Poublanc J, Crawley A P, Stainsby J A, Fisher J A, & Mikulis D J (2008). Mapping cerebrovascular reactivity using blood oxygen level-dependent MRI in Patients with arterial steno-occlusive disease: comparison with arterial spin labeling MRI. *Stroke* 39, 2021-2028.

Mark C I, Slessarev M, Ito S, Han J, Fisher J A, & Pike G B (2010). Precise control of end-tidal carbon dioxide and oxygen improves BOLD and ASL cerebrovascular reactivity measures. *Magn Reson Med*.

Markus H & Cullinane M (2001). Severely impaired cerebrovascular reactivity predicts stroke and TIA risk in patients with carotid artery stenosis and occlusion. *Brain* 124, 457-467.

Markus H S & Harrison M J (1992). Estimation of cerebrovascular reactivity using transcranial Doppler, including the use of breath-holding as the vasodilatory stimulus 6. *Stroke* 23, 668-673.

Mikulis D J, Krolczyk G, Desal H, Logan W, Deveber G, Dirks P, Tymianski M, Crawley A, Vesely A, Kassner A, Preiss D, Somogyi R, & Fisher J A (2005). Preoperative and postoperative mapping of cerebrovascular reactivity in moyamoya disease by using blood oxygen level-dependent magnetic resonance imaging. *J Neurosurg* 103, 347-355.

Nishimura S, Suzuki A, Hatazawa J, Nishimura H, Shirane R, Yasui N, & Yoshimoto T (1999). Cerebral blood-flow responses to induced hypotension and to CO2 inhalation in patients with major cerebral artery occlusive disease: a positron-emission tomography study. *Neuroradiology* 41, 73-79.

Ogasawara K, Ogawa A, & Yoshimoto T (2002). Cerebrovascular reactivity to acetazolamide and outcome in patients with symptomatic internal carotid or middle cerebral artery occlusion: a xenon-133 single-photon emission computed tomography study. *Stroke* 33, 1857-1862.

Prisman E, Slessarev M, Han J, Poublanc J, Mardimae A, Crawley A, Fisher J, & Mikulis D (2007). Comparison of the effects of independently-controlled end-tidal PCO(2) and PO(2) on blood oxygen level-dependent (BOLD) MRI. *J Magn Reson Imaging*.

Ringelstein E B, Sievers C, Ecker S, Schneider P A, & Otis S M (1988). Noninvasive assessment of CO2-induced cerebral vasomotor response in normal individuals and patients with internal carotid artery occlusions. *Stroke* 19, 963-969.

Sasse S A, Berry R B, Nguyen T K, Light R W, & Mahutte C K (1996). Arterial blood gas changes during breath-holding from functional residual capacity. *Chest* 110, 958-964.

Silvestrini M, Vernieri F, Troisi E, Passarelli F, Matteis M, Pasqualetti P, Rossini P M, & Caltagirone C (1999a). Cerebrovascular reactivity in carotid artery occlusion: possible implications for surgical management of selected groups of patients. *Acta Neurol Scand* 99, 187-191.

Silvestrini M, Vernieri F, Troisi E, Passarelli F, Matteis M, Pasqualetti P, Rossini P M, & Caltagirone C (1999b). Cerebrovascular reactivity in carotid artery occlusion: possible implications for surgical management of selected groups of patients 17. *Acta Neurol Scand* 99, 187-191.

van der Zande F H, Hofman P A, & Backes W H (2005). Mapping hypercapnia-induced cerebrovascular reactivity using BOLD MRI 1. *Neuroradiology* 47, 114-120.

Vorstrup S, Brun B, & Lassen N A (1986). Evaluation of the cerebral vasodilatory capacity by the acetazolamide test before EC-IC bypass surgery in patients with occlusion of the internal carotid artery. *Stroke* 17, 1291-1298.

Webb J, Guimond A, Eldridge P, Chadwick D, Meunier J, Thirion J P, & Roberts N (1999). Automatic detection of hippocampal atrophy on magnetic resonance images. *Magn Reson Imaging* 17, 1149-1161.

Yonas H, Smith H A, Durham S R, Pentheny S L, & Johnson D W (1993). Increased stroke risk predicted by compromised cerebral blood flow reactivity. *J Neurosurg* 79, 483-489.

SUPPLEMENTAL REFERENCE LIST

Sobczyk O, Battisti-Charbonney A, Fierstra J, Mandell D M, Poublanc J, Crawley A P, Mikulis D J, Duffin J, Fisher J A., A conceptual model for CO2-induced redistribution of cerebral blood flow with experimental confirmation using BOLD MRI. Neuroimage. 2014 Feb. 5; 92C:56-68.

Y. C. Tzeng, P. N. Ainslie, W. H. Cooke, K. C. Peebles, C. K. Willie, B. A. MacRae, J. D. Smirl' H. M. Horsman, and C. A. Rickards. Assessment of cerebral autoregulation: the quandary of quantification. Am J Physiol Heart Circ Physiol 303: H658-H671, 2012.

We claim:

1. A method of assessing an abnormality in a test subject's vascular response to a vasoactive stimulus, the method comprising:
imposing at least one standardized change in arterial partial pressure of carbon dioxide in the test subject using a sequential gas delivery circuit, the at least one standardized change comprising a step change;

measuring test subject vascular response signals using a magnetic resonance imaging device, the test subject vascular response signals comprising at least a time course representing the test subject's vascular response to the at least one standardized change in arterial partial pressure of carbon dioxide in at least one region of interest of the test subject's brain;

calculating a score for the test subject, the score representing a comparison between the test subject vascular response signals for individual voxels in the at least one region of interest and respective computed statistical values per corresponding voxel, the respective computed statistical values representing a normal distribution of vascular response signals in a plurality of control subjects;

wherein the respective computed statistical values per corresponding voxel are computed based on a set of vascular response signals obtained for the plurality of control subjects, each vascular response signal representing a vascular response to at least one standardized change in arterial partial pressure of carbon dioxide per voxel in at least one common region of interest of each control subject's brain, the respective voxel coordinates co-registered to a standardized space based on a set of anatomic landmarks;

wherein the at least one standardized change in arterial partial pressure of carbon dioxide in the at least one region of interest of the test subject's brain is approximately the same as the at least one standardized change in arterial partial pressure of carbon dioxide per voxel in the at least one common region of interest of each control subject's brain; and wherein the respective computed statistical values per corresponding voxel are computed by calculating a mean and a standard deviation of the vascular responses per voxel;

determining a probability that the test subject's vascular response is abnormal based on the score;

mapping the score onto an anatomical representation of the standardized space to generate a statistical map of the test subject's vascular response to the vasoactive stimulus; and depicting, on a voxel by voxel basis, the probability that the test subject's vascular response is abnormal on the statistical map.

2. The method of claim 1, wherein each vascular response signal is quantifiable from a surrogate measure of blood flow.

3. The method of claim 2, wherein the surrogate measure of blood flow comprises a high temporal resolution measure of the amplitude of a change in blood flow, expressed as a time constant of a change in blood flow.

4. The method of claim 1, wherein the co-registered voxel coordinates are full brain voxel coordinates defining a set of potential regions of interest.

5. The method of claim 1, wherein the at least one standardized change in arterial partial pressure of carbon dioxide in the test subject's brain is a vasodilatory stimulus.

6. The method of claim 5, wherein the vasodilatory stimulus is at least one targeted increase in the subject's end tidal partial pressure of carbon dioxide from a steady state baseline value or previously targeted arterial partial pressure of carbon dioxide.

7. The method of claim 5, wherein the vasodilatory stimulus is a ramp sequence.

8. The method of claim 1, wherein the test subject's vascular response is a cerebrovascular response (CVR), wherein the surrogate measure of blood flow is a change in a blood oxygen level dependent magnetic resonance imaging ($\Delta S$) to a targeted increase in the test subject's end tidal $PCO_2$ ($P_{ET}CO_2$), and wherein $CVR=\Delta S/\Delta P_{ET}CO_2$.

9. The method of claim 1, wherein the plurality of control subjects are selected on the basis that the plurality of control subjects report being free of neurological disease.

10. The method of claim 1, wherein the plurality of control subjects are selected to provide control data for selected parameters of the test subject.

11. The method of claim 10, wherein the selected parameters include one or more of: age, sex, oxygen consumption, capillary density, changes in blood volume, differences in blood arrival time, vascular response time, genetic makeup, variations in diet, sleep pattern, time of day, hormonal level, physical fitness, blood pressure, blood pressure response to hypercapnia, state of mind, medication, prior medical treatment, prior illness, or medical condition.

12. The method of claim 1, further comprising calculating the score relative to the respective means and standard deviations per corresponding voxel, as z values.

13. The method of claim 12, further comprising color-coding the z values and mapping the color-coded values back onto an anatomical representation of the standardized space to produce a z map.

14. The method of claim 1, further comprising:
re-testing each control subject at least once after an interval at each arterial partial pressure of carbon dioxide to obtain a second set of vascular response signals representing at least one additional measurement of each control subject's control re-test vascular response per voxel;
computing a value representing a control difference between the respective vascular response and control re-test vascular response per voxel and per control subject;
wherein computing a set of statistical values of the vascular responses comprises computing statistical values for the control differences;
obtaining a re-test test subject vascular response signals representing the test subject's re-test vascular response; and
scoring a difference between the test subject's test vascular response and the test subject's re-test vascular response for respective voxels relative to the set of statistical values per corresponding voxel.

15. The method of claim 14, wherein at least one value representing the set of statistical values in the vascular response per voxel includes a voxel mean and voxel standard deviation wherein the differences between the subject's test response and re-test response for respective voxels corresponding to the at least one region of interest are scored, relative to the voxel means and standard deviations, using z values.

16. The method of claim 14 wherein at least one value representing the set of statistical values in the vascular response per voxel includes a voxel mean and standard deviation with respect to the quantum and variability of the respective differences between the test and re-test vascular response values for the plurality of control subjects.

17. The method of claim 14 wherein the differences between the subject's test response and re-test response for respective voxels corresponding to the at least one region of interest are scored, relative to the respective means and standard deviation of the respective computed differences, using z values.

18. The method of claim 17 further comprising generating an anatomical map of the subject's brain, wherein each voxel is assigned a color corresponding to the z value of the respective voxel.

19. A system for assessing an abnormality in a test subject's vascular response to a vasoactive stimulus, the system comprising:
 a sequential gas delivery circuit for generating at least one standardized change in arterial partial pressure of carbon dioxide in at least one region of interest of the test subject's brain;
 a magnetic resonance imaging system for measuring test subject vascular response signals, the subject vascular response signals comprising at least a time course representing the test subject's vascular response to the at least one standardized change in arterial partial pressure of carbon dioxide in the at least one region if interest of the test subject's brain; and
 a processor connected to the sequential gas delivery circuit and the magnetic resonance imaging system, the processor configured to:
  calculate a score for the test subject, the score representing a comparison between the test subject vascular response signals for individual voxels in the at least one region of interest and respective computed statistical values per corresponding voxel, the computed statistical values representing a normal distribution of vascular response signals in a plurality of control subjects;
  wherein the respective computed statistical values per corresponding voxel are computed based on a set of vascular response signals obtained for the plurality of control subjects, each vascular response signal representing a vascular response to at least one standardized change in arterial partial pressure of carbon dioxide per voxel in at least one common region of interest of each control subject's brain, the respective voxel coordinates co-registered to a standardized space based on a set of anatomic landmarks;
  wherein the at least one standardized change in arterial partial pressure of carbon dioxide in the at least one region of interest of the test subject's brain is approximately the same as the at least one standardized change in arterial partial pressure of carbon dioxide per voxel in the at least one common region of interest of each control subject's brain; and
  wherein the respective computed statistical values per corresponding voxel are computed by calculating a mean and a standard deviation of the vascular responses per voxel; and
 determine a probability that the test subject's vascular response is abnormal based on the score;
 map the score onto an anatomical representation of the standardized space to generate a statistical map of the test subject's vascular response to the vasoactive stimulus; and
 depict, on a voxel by voxel basis, the probability that the test subject's vascular response is abnormal on the statistical map.

* * * * *